US008118835B2

(12) United States Patent
Weisel et al.

(10) Patent No.: US 8,118,835 B2
(45) Date of Patent: Feb. 21, 2012

(54) SUTURE ANCHOR

(75) Inventors: Thomas Weisel, Ventura, CA (US);
Martin Padget, Valencia, CA (US);
David Skinlo, Ventura, CA (US); Brett Bannerman, Canyon Country, CA (US)

(73) Assignee: Surgical Solutions, LLC, Valencia, CA (US)

( * ) Notice: Subject to any disclaimer, the term of this patent is extended or adjusted under 35 U.S.C. 154(b) by 1401 days.

(21) Appl. No.: 11/238,801

(22) Filed: Sep. 28, 2005

(65) Prior Publication Data

US 2006/0106423 A1 May 18, 2006

Related U.S. Application Data

(60) Provisional application No. 60/613,877, filed on Sep. 28, 2004.

(51) Int. Cl.
*A61B 17/04* (2006.01)
(52) U.S. Cl. ........................................ 606/232; 606/300
(58) Field of Classification Search .................. 606/232, 606/213, 215, 139, 144, 228
See application file for complete search history.

(56) References Cited

U.S. PATENT DOCUMENTS

| 5,203,787 A | 4/1993 | Noblitt et al. |
| 5,236,445 A | 8/1993 | Hayhurst et al. |
| 5,324,308 A | 6/1994 | Pierce |
| 5,383,905 A | 1/1995 | Golds et al. |
| 5,405,359 A | 4/1995 | Pierce |
| 5,486,197 A | 1/1996 | Le et al. |
| 5,522,844 A | 6/1996 | Johnson |
| 5,534,011 A | 7/1996 | Greene, Jr. et al. |
| 5,545,180 A | 8/1996 | Le et al. |
| 5,550,023 A | 8/1996 | Kinzler et al. |
| 5,584,835 A | 12/1996 | Greenfield |
| 5,591,207 A | 1/1997 | Coleman |
| 5,662,683 A | 9/1997 | Kay |
| 5,702,397 A | 12/1997 | Goble et al. |
| 5,709,708 A | 1/1998 | Thal |
| 5,720,766 A | 2/1998 | Zang et al. |
| 5,728,136 A | 3/1998 | Thal |
| 5,782,864 A | 7/1998 | Lizardi |
| 5,810,854 A | 9/1998 | Beach |
| 5,814,070 A | 9/1998 | Borzone et al. |
| 5,814,071 A | 9/1998 | McDevitt et al. |
| 5,879,372 A | 3/1999 | Bartlett |
| 5,899,920 A | 5/1999 | DeSatnick et al. |
| 5,902,321 A | 5/1999 | Caspari et al. |
| 5,981,168 A | 11/1999 | Reiner et al. |
| 6,024,758 A | 2/2000 | Thal |
| 6,045,574 A | 4/2000 | Thal |

(Continued)

*Primary Examiner* — Tuan Nguyen
(74) *Attorney, Agent, or Firm* — Myers Andras Sherman & Zarrabian LLP; Joseph C. Andras

(57) ABSTRACT

A suture anchor (e.g. 100) for knotlessly securing nearby tissue to bone is formed from an anchor body (e.g. 101/102) that includes a mechanism for being securely anchored to the bone, an elongated suture puller (e.g. 122) extending through the anchor body with a proximal end for being pulled in a proximal direction by a surgeon and a distal end (e.g. 125) with a suitable mechanism for engaging suture (e.g. 127), suture (e.g. 132) carried by the engaging mechanism (e.g. 127) at the distal end (e.g. 125) of the elongated suture puller (e.g. 122), and a suture locking mechanism (e.g. 110) that substantially prevents the suture (e.g. 122) from moving in at least a first direction after being pulled into and through the anchor body (e.g. 101/102) by the elongated suture puller (e.g. 122).

10 Claims, 21 Drawing Sheets

U.S. PATENT DOCUMENTS

| | | |
|---|---|---|
| 6,066,160 A | 5/2000 | Colvin et al. |
| 6,143,017 A | 11/2000 | Thal |
| 6,200,329 B1 | 3/2001 | Fung et al. |
| 6,206,886 B1 | 3/2001 | Bennett |
| 6,267,766 B1 | 7/2001 | Burkhart |
| 6,520,980 B1 | 2/2003 | Foerster |
| 6,544,267 B1 | 4/2003 | Cole et al. |
| 6,554,852 B1 | 4/2003 | Oberlander |
| 6,582,453 B1 | 6/2003 | Tran et al. |
| 6,592,609 B1 | 7/2003 | Bonutti |
| 6,641,596 B1 | 11/2003 | Lizardi |
| 6,652,561 B1 | 11/2003 | Tran |
| 6,666,877 B2 | 12/2003 | Morgan et al. |
| 6,689,154 B2 | 2/2004 | Bartlett |
| 7,090,690 B2 * | 8/2006 | Foerster et al. ............. 606/232 |
| 7,416,556 B2 * | 8/2008 | Jackson ...................... 606/232 |
| 2001/0018593 A1 | 8/2001 | Nguyen et al. |
| 2002/0004668 A1 | 1/2002 | Bartlett |
| 2002/0004669 A1 | 1/2002 | Bartlett |
| 2002/0007196 A1 | 1/2002 | Bartlett |
| 2002/0095180 A1 | 7/2002 | West et al. |
| 2002/0111653 A1 | 8/2002 | Foerster |
| 2002/0128684 A1 | 9/2002 | Foerster |
| 2003/0004545 A1 | 1/2003 | Burkhart et al. |
| 2003/0088250 A1 | 5/2003 | Colleran et al. |
| 2003/0109900 A1 | 6/2003 | Martinek |
| 2003/0120694 A1 | 6/2003 | Qi |
| 2003/0149448 A1 | 8/2003 | Foerster et al. |
| 2003/0149449 A1 | 8/2003 | Friden |
| 2003/0195563 A1 | 10/2003 | Foerster |
| 2003/0195564 A1 | 10/2003 | Tran |
| 2004/0039404 A1 | 2/2004 | Dreyfuss |
| 2004/0098050 A1 | 5/2004 | Foerster et al. |
| 2004/0098051 A1 | 5/2004 | Fallin et al. |
| 2004/0098052 A1 | 5/2004 | West et al. |
| 2004/0098053 A1 | 5/2004 | Tran |
| 2004/0133239 A1 | 7/2004 | Singhatat |
| 2004/0138683 A1 | 7/2004 | Shelton et al. |
| 2004/0138706 A1 | 7/2004 | Abrams et al. |
| 2004/0153103 A1 | 8/2004 | Schwartz et al. |
| 2004/0167576 A1 | 8/2004 | Pedlick et al. |
| 2005/0245932 A1 * | 11/2005 | Fanton et al. ................. 606/72 |
| 2006/0282081 A1 * | 12/2006 | Fanton et al. ................. 606/72 |

* cited by examiner

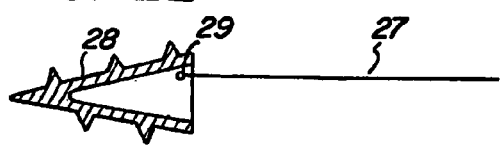
FIG. 22
FIG. 23
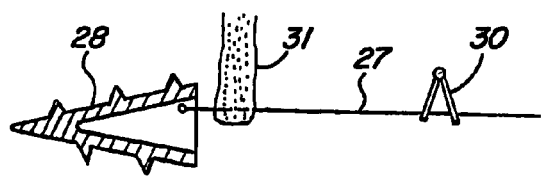
FIG. 24
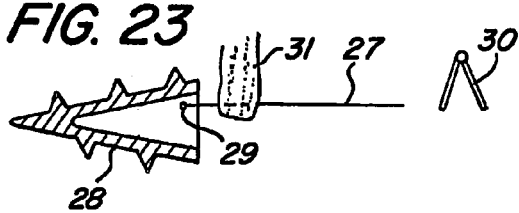
FIG. 25
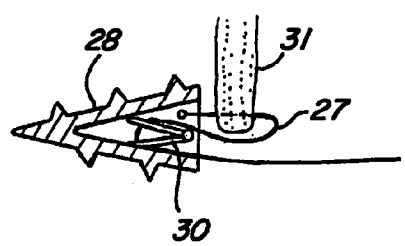
FIG. 26
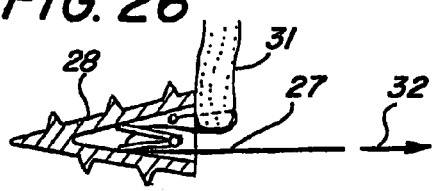
FIG. 27
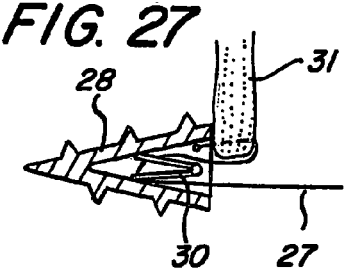

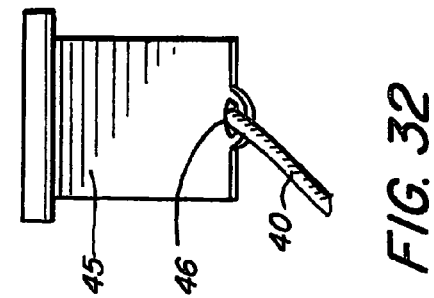
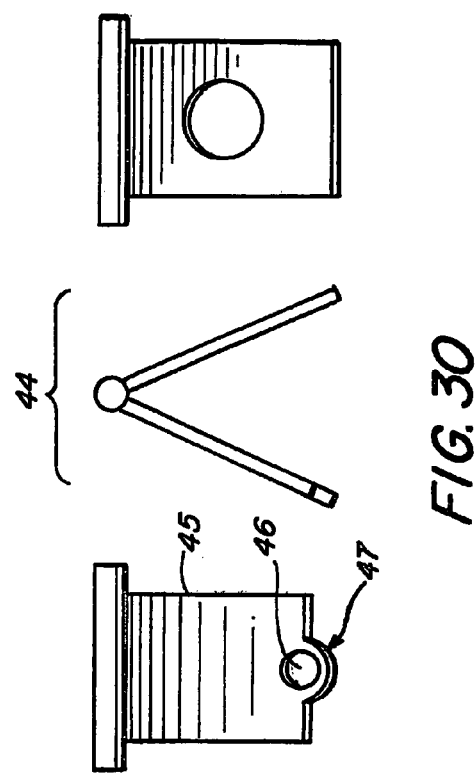
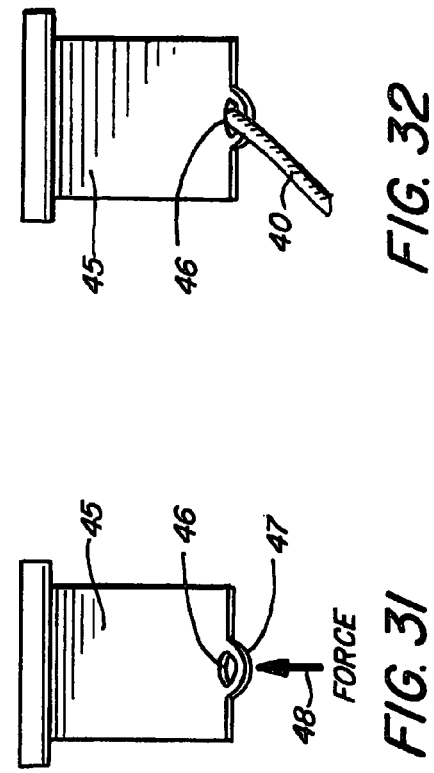
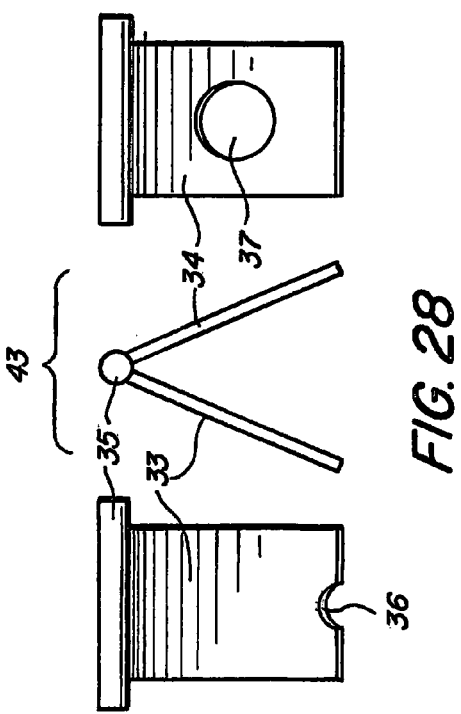
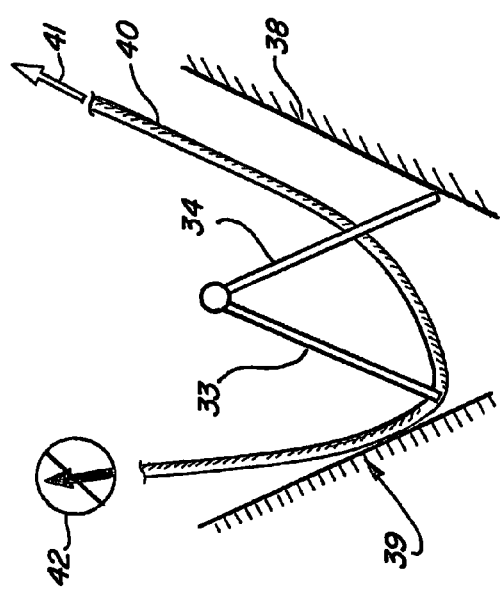

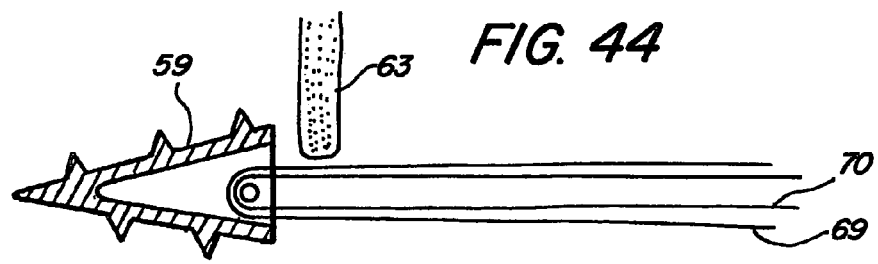
FIG. 44
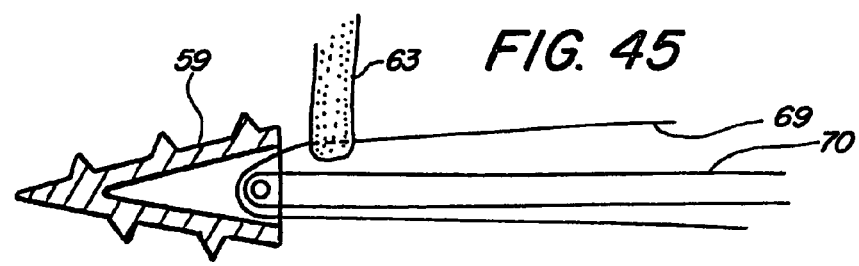
FIG. 45
FIG. 46
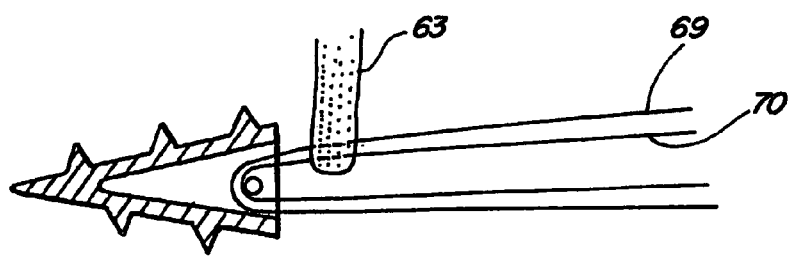
FIG. 47
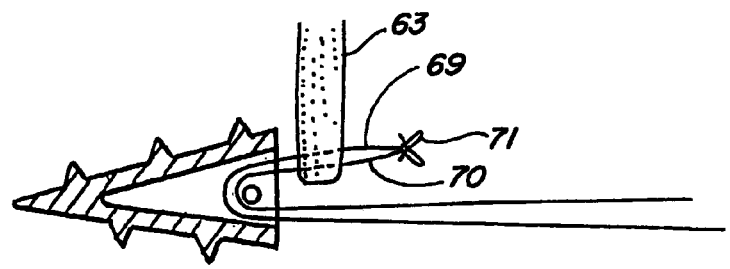

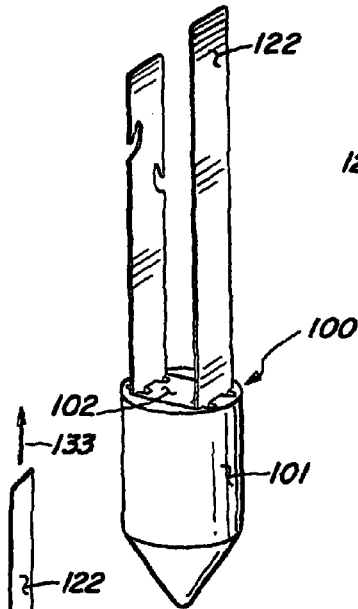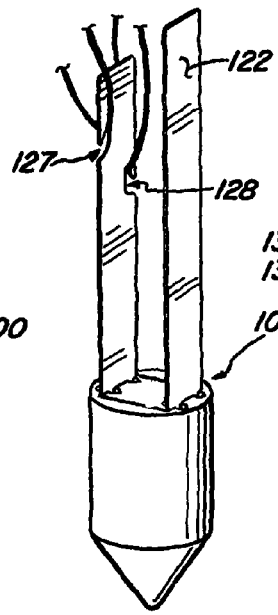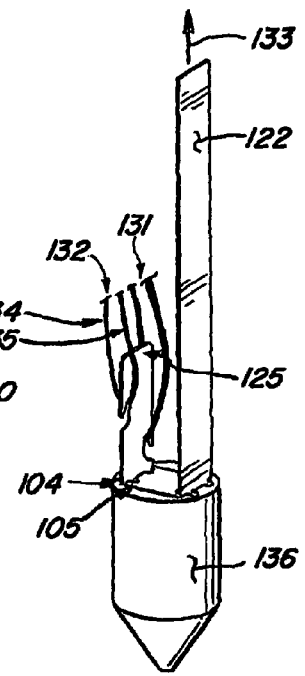
FIG. 63  FIG. 64  FIG. 65
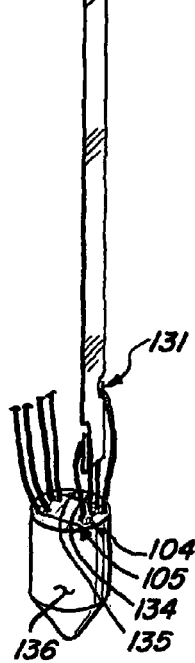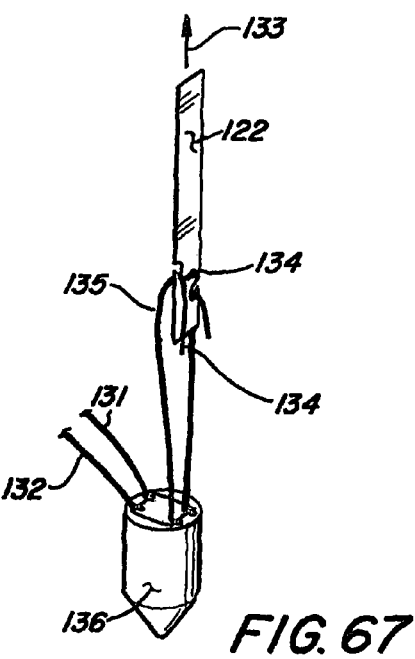
FIG. 66  FIG. 67

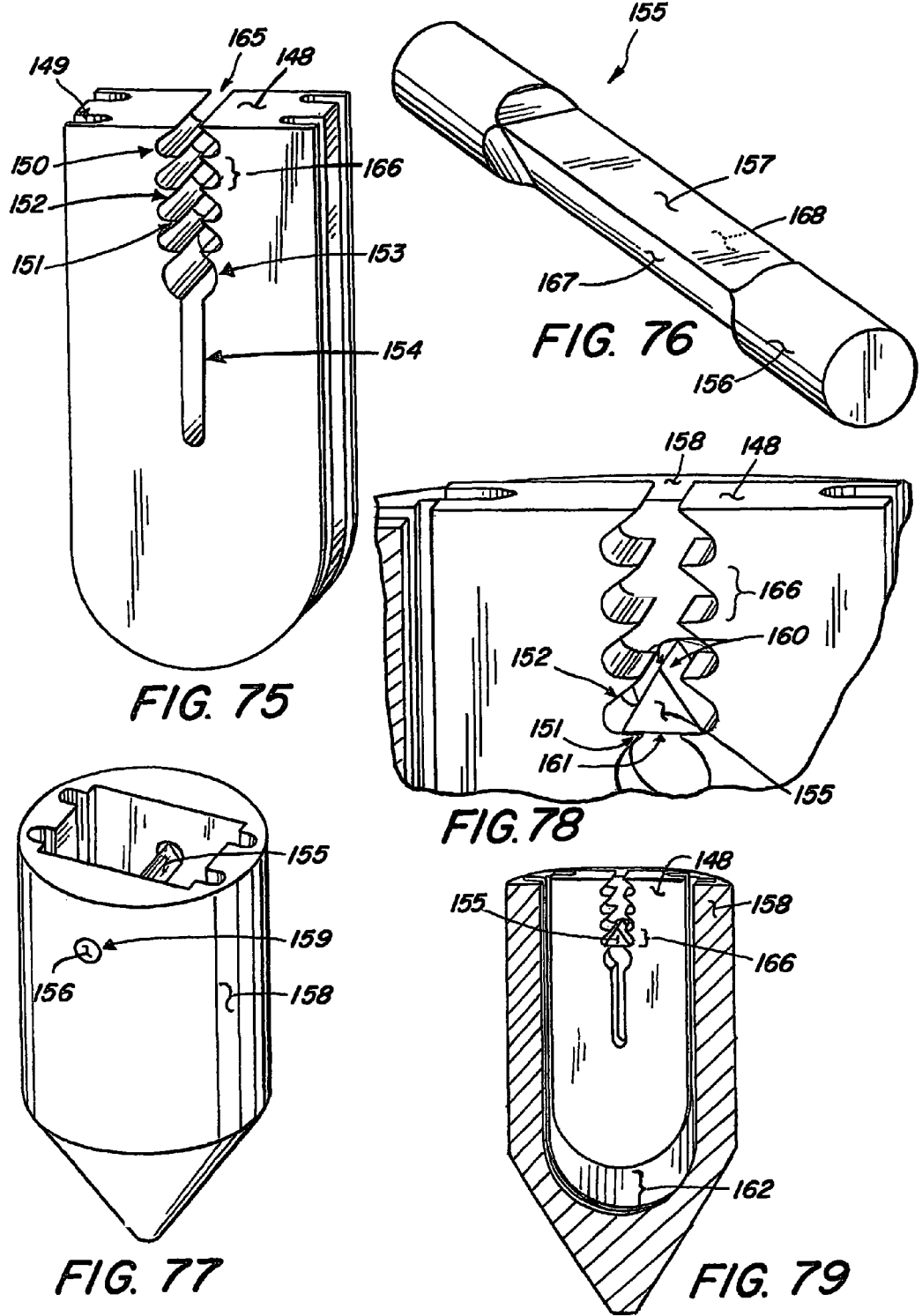

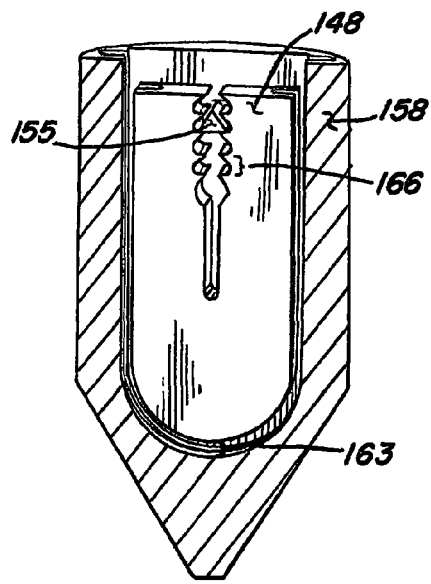
FIG. 80
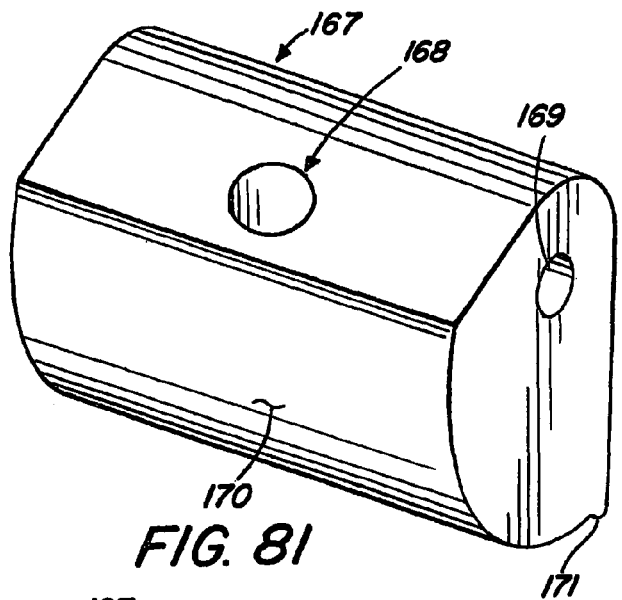
FIG. 81
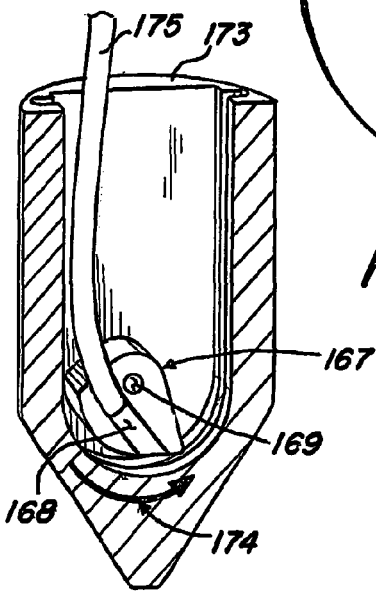
FIG. 83
FIG. 82
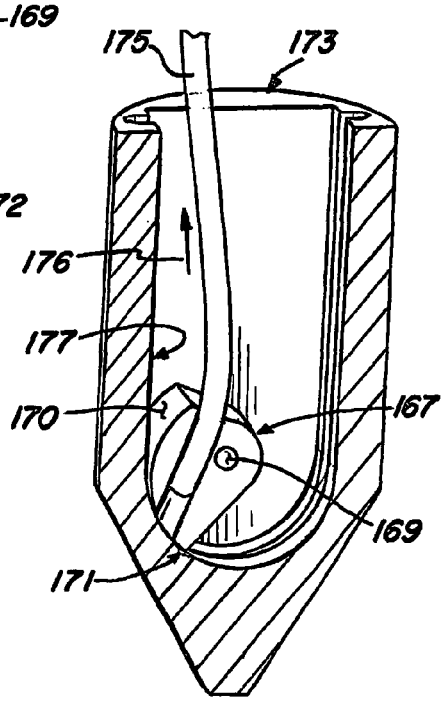
FIG. 84

SUTURE ANCHOR

CROSS REFERENCE TO RELATED APPLICATIONS

This application claims the benefit of Provisional Application Ser. No. 60/613,877 filed on Sep. 28, 2004, entitled "SUTURE ANCHOR," which application is fully incorporated herein by reference.

BACKGROUND OF THE INVENTION

1. Field of the Invention

This invention relates generally to surgical fixation devices and, more specifically, to medical implants known as suture anchors that are used to attach soft tissue to hard tissue via a strand of suture in order to implement a repair. The following disclosure presents several suture anchor designs that will greatly simplify the attachment step of this repair by eliminating the need to create a knot.

2. Discussion of Related Art

A common surgical procedure is to repair an injury by re-attaching soft tissue to bone. This surgical attachment is required to hold the soft and hard tissues together until the body's natural healing response permanently attaches the two together.

There are many styles of anchors currently on the market. Most require the anchor to be implanted into bone with suture already threaded through an eyelet thereof, the strand of suture to be passed through soft tissue, and then a knot to be tied so that the soft tissue is brought adjacent to the bone for proper healing. The last step, knot tying, is very critical and for many surgeons one of the more difficult steps. This is especially true for the doctor performing the procedure arthroscopically where everything is viewed on a monitor via a camera and most of the work is performed through small diameter cannulas.

Some anchors systems have been released in the past few years that attempt to address the difficult knot tying issue. Though they have created a knotless system many of the methods are cumbersome. A knotless design that is easy and intuitive is required.

SUMMARY OF THE INVENTION

In one aspect, the invention is a suture anchor for securing nearby tissue to bone, the suture anchor comprising an anchor body having an axis and a proximal end that is substantially transverse to the axis; means for anchoring the anchor body to the bone of the patient; an elongated suture puller slidably located in the anchor body with first and second lengths extending therefrom, the second length including means for engaging suture; suture connected to the second length of the elongated suture puller via the means for engaging whereby the suture may be pulled into and through the anchor body behind the elongated suture puller when the elongated suture puller is pulled outward therefrom via the first length; and a suture locking mechanism that substantially prevents the suture from moving in at least a first direction after being pulled into and through the anchor body by the elongated suture puller.

These and other features and advantages of the invention will become more apparent with a description of preferred embodiments in reference to the associated drawings.

DESCRIPTION OF THE DRAWINGS

First Embodiment

FIG. 1 shows a screw-in style anchor having an integral suture locking mechanism with a suture puller passing therethrough, and having one end of a strand of suture affixed thereto (optional);

FIG. 2 shows the suture being passed through a piece of tissue;

FIG. 3 shows the suture being threaded though a loop at the end of the suture puller;

FIG. 4 shows the suture puller being used to draw the suture toward the suture anchor's suture locking mechanism;

FIG. 5 shows the suture being pulled through the suture anchor's suture locking mechanism;

FIG. 6 shows the suture drawing the tissue toward the suture anchor at a desired tension;

FIG. 7 shows the suture after it has been trimmed by the surgeon;

Second Embodiment

Figure 8:
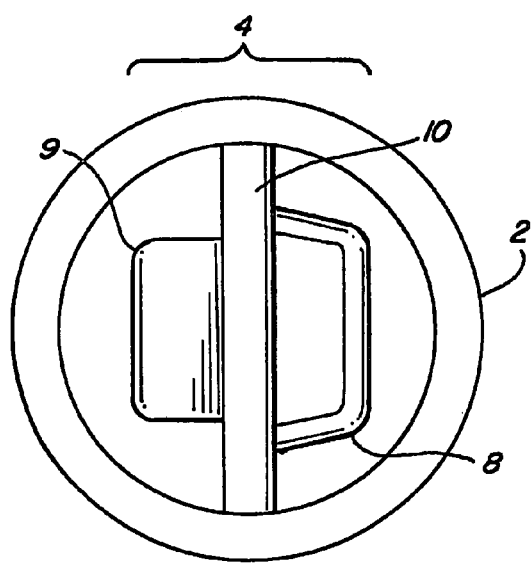
Figure 10:
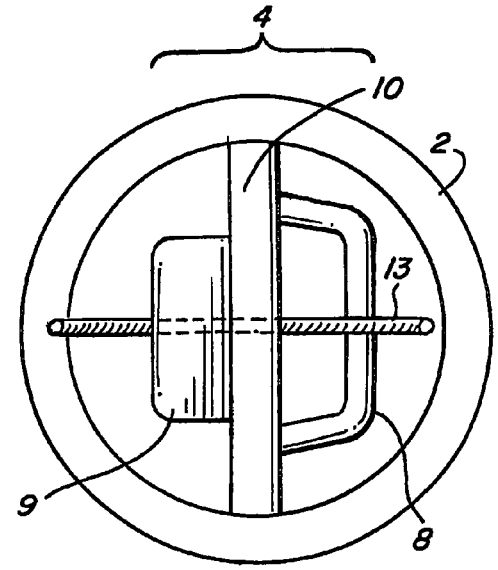
Figure 9:
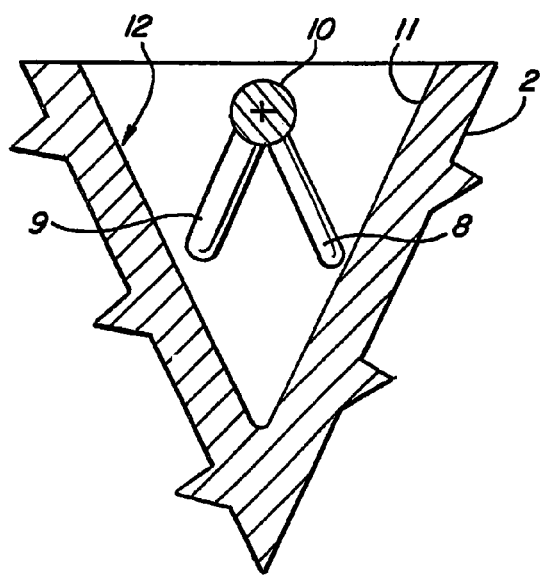
Figure 11:
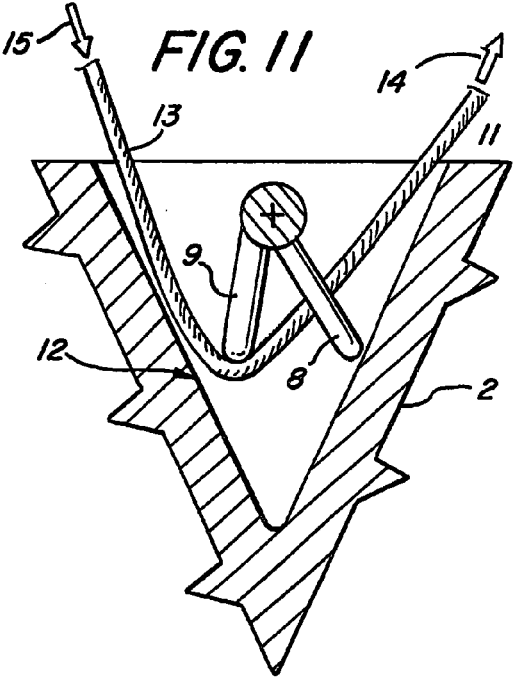
Figure 12:
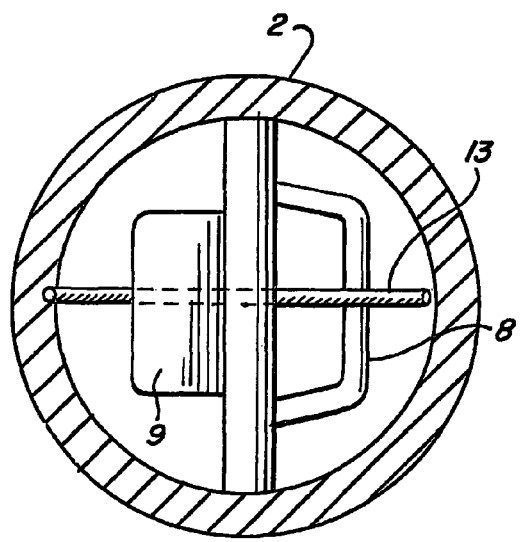
Figure 13:
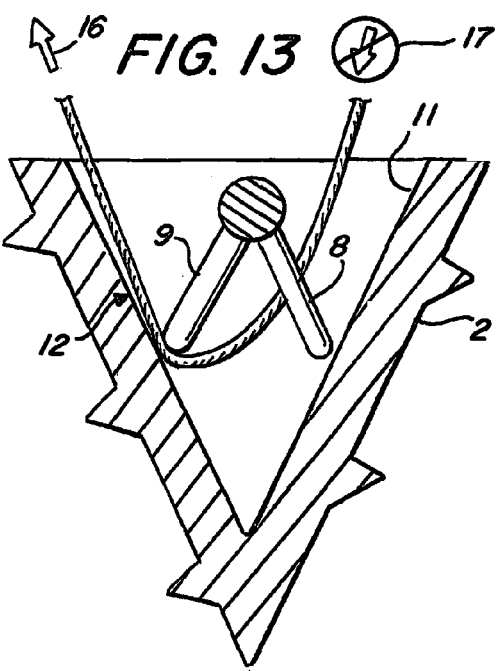

FIGS. 8-13 show an embodiment of a suture anchor having a particular locking mechanism that is formed from a pivoting member that is biased against an inner wall of the suture anchor with a bent spring that contacts an opposite wall of the suture anchor;

FIGS. 8-9 show the suture anchor without the suture yet present;

FIG. 8 is a top view of a suture anchor with a locking mechanism formed from a spring, a locking paddle, and a connecting member;

FIG. 9 is a cutaway side view of the suture anchor of FIG. 8;

FIGS. 10-11 are similar to FIGS. 8-9 but with the suture being pulled in one direction;

FIG. 10 is the same as FIG. 8 but with the suture present;

FIG. 11 is the same as FIG. 9 with the suture being pulled through the locking mechanism in a direction represented by the arrows;

FIGS. 12-13 are similar to FIGS. 8-9 but with the suture being pulled in an opposite direction;

FIG. 12 is the same as FIG. 8 but with the suture present;

FIG. 13 is the same as FIG. 9 showing the suture being pulled in the opposite direction will result in little or minimal movement due to the locking paddle;

Third Embodiment

Figure 14:
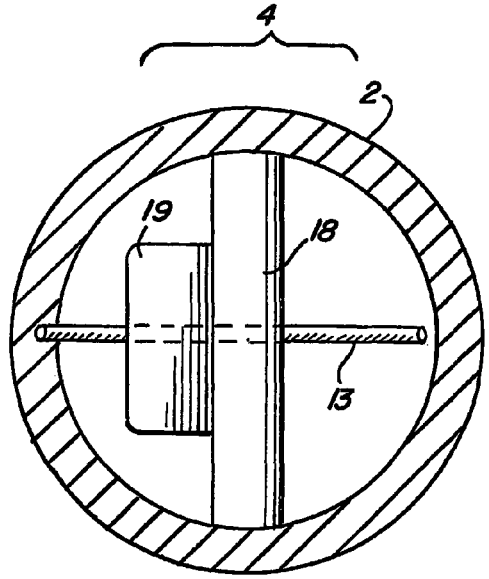
Figure 15:
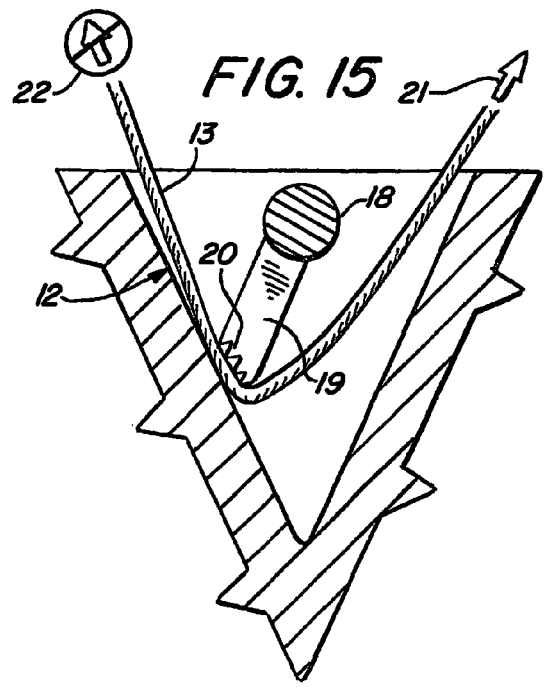
Figure 16:
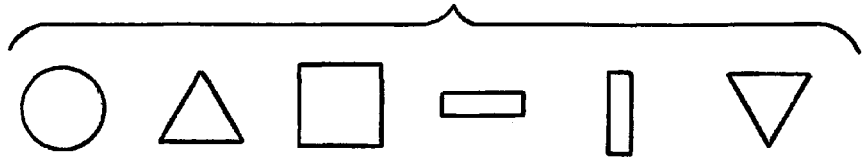

FIGS. 14-16 relate to a third embodiment of a suture anchor having another particular locking mechanism that is formed from a pivoting member, but here the spring is a torsional spring;

FIG. 14 shows a top plan view of suture anchor with suture present;

FIG. 15 is a cutaway side view of the suture anchor of FIG. 14, and also shows a roughened surface that comes into contact with the suture in order to enhance the effectiveness of the suture locking mechanism;

FIG. 16 shows several alternative cross-sectional profiles for a torsional spring used in suture anchor of FIGS. 14 and 15;

Fourth Embodiment

Figure 17:
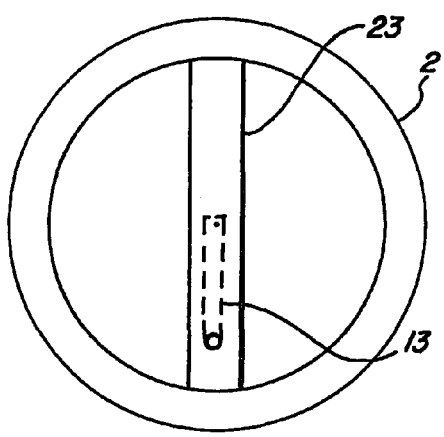
Figure 18:
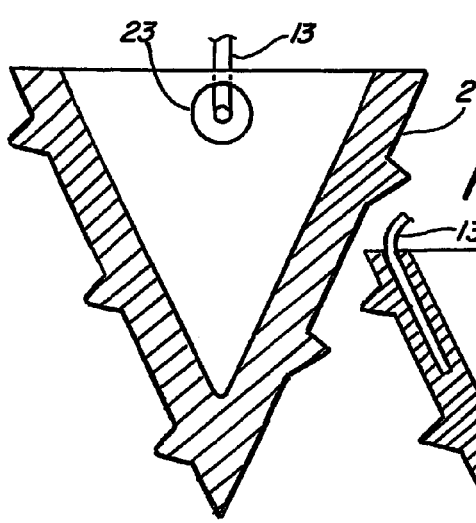

FIGS. 17-18 show an embodiment of how one end of a suture strand may be affixed to the anchor body of a suture anchor;

FIG. 17 is a top view of an anchor body with a cross pin present in order to hold a suture strand therein and extending from one side thereof;

FIG. 18 is a cutaway side view of the anchor body of FIG. 17 showing the suture strand within and extending from the cross pin;

Fifth Embodiment

Figure 19A:
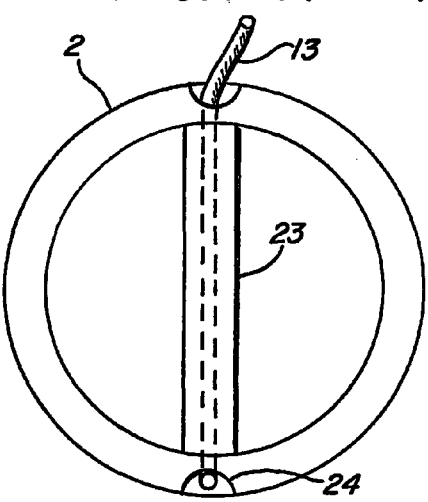
Figure 19B:
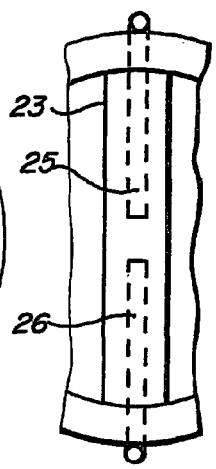
Figure 20:
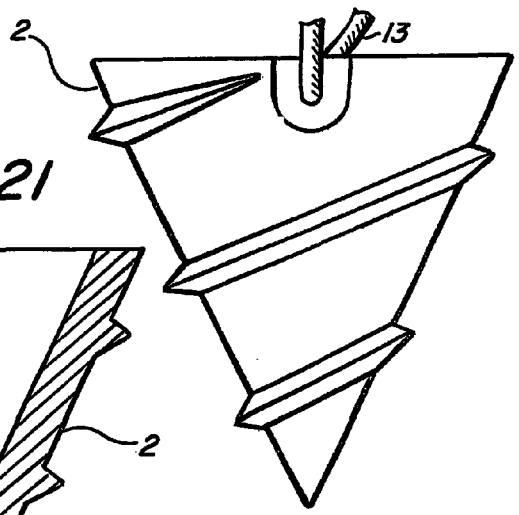

FIGS. 19A, 19B, and 20 show a variation on the embodiment FIGS. 17-18 wherein two strands of suture are affixed to the anchor body;

FIG. 19A is a top view of an anchor body with a cross pin present in order to hold a suture strand therein and extending from both sides thereof, and also showing an optional notch that provides relief for the suture to turn upward after extending outward from the cross pin;

FIG. 19B is similar to FIG. 19A, but two separate strands have been affixed to the anchor body with the cross pin;

FIG. 20 is a is a cutaway side view of the anchor body of FIG. 19A showing the suture strands within and extending from the cross pin, and also showing the optional notch;

Sixth Embodiment

Figure 21:
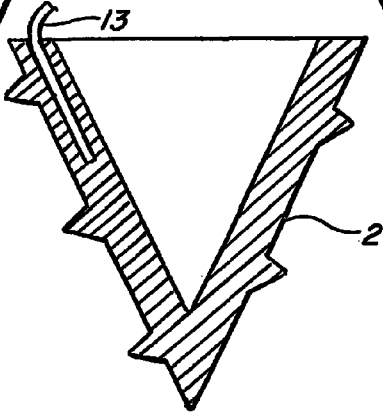

FIG. 21 is an embodiment of how one end of a suture strand may be affixed to the anchor body by being placed directly in the wall of the Anchor Body

Seventh Embodiment

Figure 1:
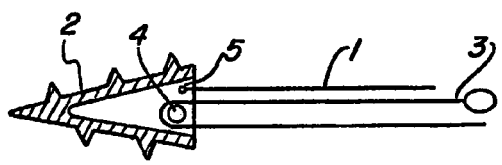
FIGS. 1-7 show an embodiment implemented within a screw-in style anchor that has one end of a strand of suture already affixed to the anchor body, and an integral suture locking mechanism.

FIGS. 22-29 show an embodiment implemented within a screw-in style anchor that has one end of a strand of suture already affixed to the anchor body (as shown in FIG. 1), but which uses a locking mechanism that is not integral with the anchor body but rather is pushed down the suture after the suture has been passed through the patient's tissue;

FIG. 22 shows a screw-in style anchor having an anchor body that is capable of receiving a suture locking mechanism, and having one end of a strand of suture affixed thereto (optional);

FIG. 23 shows the suture being passed through a piece of tissue;

FIG. 24 shows a suture locking mechanism comprising a spring-loaded anchor clip being slid down the suture;

FIG. 25 shows the anchor clip being attached to the anchor body;

FIG. 26 shows the suture being pulled in a direction such that the suture weaves through the anchor clip and pulls the tissue toward the anchor body at a desired tension;

FIG. 27 shows the suture after it has been trimmed by the surgeon;

FIG. 28 shows three views of the anchor clip used in the embodiment illustrated by FIGS. 22-27, this particular anchor clip having a pinching notch on a paddle side thereof;

FIG. 29 is a cutaway side view showing how the anchor clip permits the suture to move in one direction but substantially prevents it from moving in the other direction;

Eighth Embodiment

Figure 33:
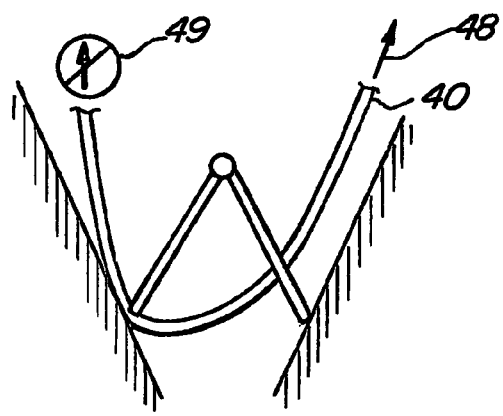

FIGS. 30-34 illustrate an alternative anchor clip that functions as suture locking mechanism that is not integral with the anchor body but rather is pushed down the suture after the suture has been passed through the patient's tissue;

FIG. 30 shows three views of the alternative anchor clip, this particular anchor clip having a pinching void on a paddle side thereof, rather than a pinching notch as shown in FIG. 28;

FIG. 31 shows how the pinching void become misshapen when a force is applied to a collapsible wall of the pinching void;

FIG. 32 shows how the misshapen pinching void can pinch a suture contained therein;

FIG. 33 is a cutaway side view showing how the anchor clip permits the suture to move in one direction but substantially prevents it from moving in the other direction;

Ninth Embodiment

Figure 34:
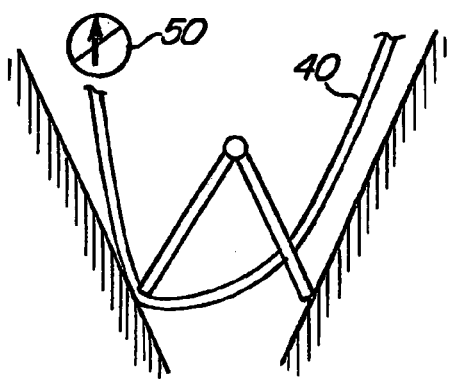
Figure 35:
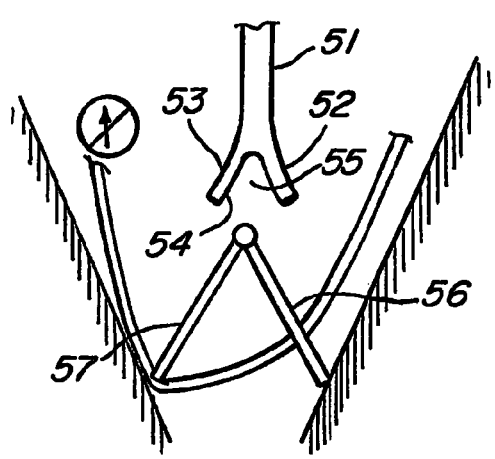
Figure 36:
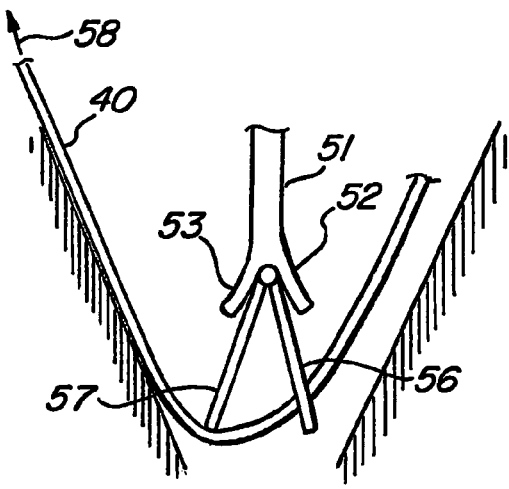

FIGS. 34-36 show a release tool that can be used to release the suture locking mechanism of FIGS. 22-29 (or FIGS. 8-13), so that suture can be temporarily slid in either direction;

FIG. 34 shows the direction in which the suture is locked and cannot move;

FIG. 35 shows a release tool having two distal arms that define a V-notch being brought toward the suture locking mechanism;

FIG. 36 shows how the release tool's distal arms collapse the suture locking mechanism by temporarily bringing the locking paddle and spring together;

Tenth Embodiment

Figure 37:
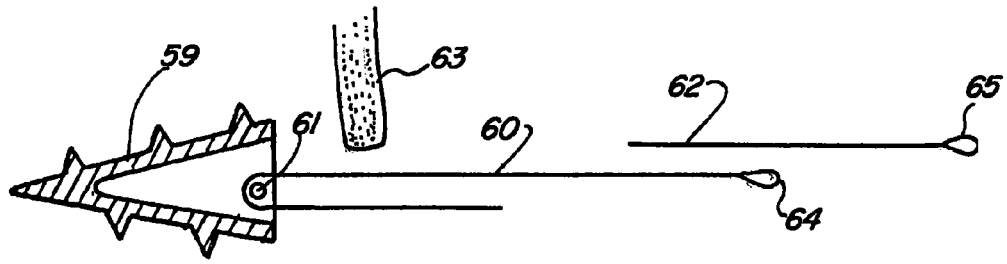
Figure 38:
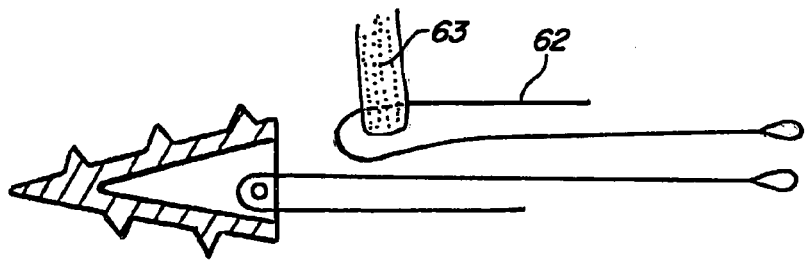
Figure 39:
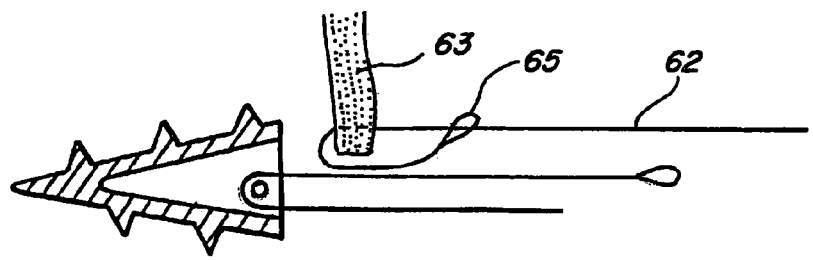
Figure 40:
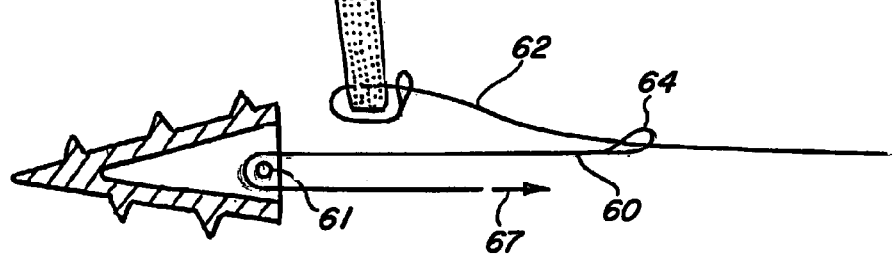
Figure 41:
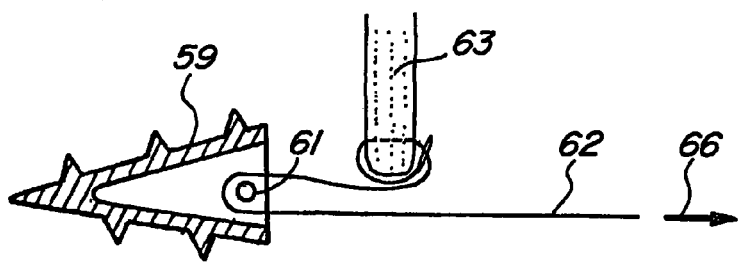
Figure 42:
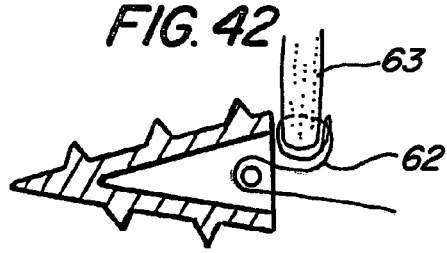

FIGS. 37-42 show an embodiment implemented within a screw-in style anchor that includes an integral suture locking mechanism comparable to the embodiment of FIGS. 1-7, but that differs from the earlier embodiment in that it is intended for use with a loose strand of suture and does not have one end of a strand of suture already affixed to the anchor body;

FIG. 37 shows a screw-in style anchor having an integral suture locking mechanism with a suture puller passing therethrough, and a loose strand of suture having a suture loop that may be used therewith illustrated nearby;

FIG. 38 shows the separate suture being passed through a piece of tissue;

FIG. 39 shows the end of the suture that was passed through the tissue passed through the suture loop at the end of the suture and the looping being pulled taught such that the suture begins to tighten against the tissue;

FIG. 40 shows the a free end of the suture that has been tightened against the tissue being threaded though a loop at the end of the suture puller so that the suture puller can pull the suture through the suture anchor's suture locking mechanism;

FIG. 41 shows the suture being pulled through the suture anchor's suture locking mechanism;

FIG. 42 shows the suture drawing the tissue toward the suture anchor at a desired tension;

Eleventh Embodiment

Figure 43A:
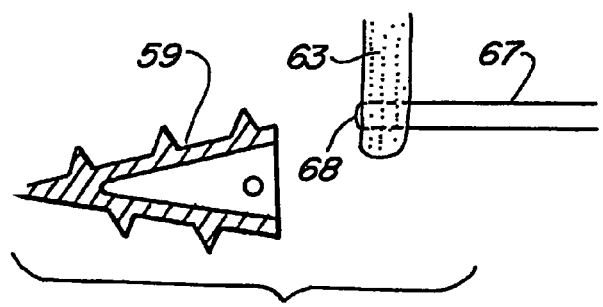
Figure 43B:
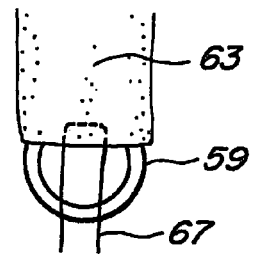

FIGS. 43A-43B illustrate an alterative embodiment for use with loose suture where not one, but two strands of suture consisting of opposite ends of the same piece of loose suture will be passed through a suitable locking mechanism;

FIG. 43A shows a loose strand of suture attached to tissue adjacent to a suture anchor, the suture having been attached to the tissue with a so-called "mattress stitch" forming a loop on one side of the tissue and with two strands extending from an opposite side of the tissue;

FIG. 43B shows how the two extending strands of suture may be passed through the mattress stitch in preparation for both strand thereafter being passed through the suture locking mechanism to draw the tissue toward the suture anchor (not shown);

Twelfth Embodiment

Figure 48:
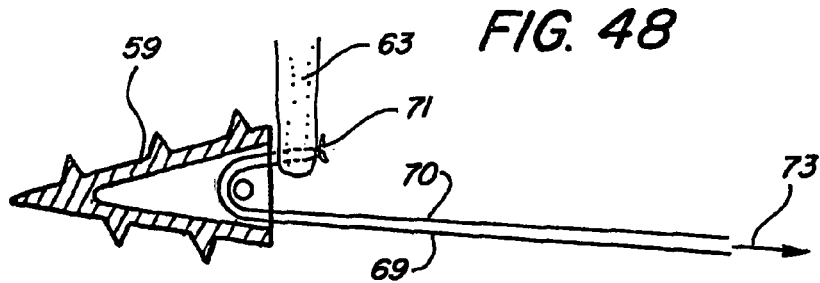

FIGS. 44-48 illustrate another alternative embodiment for use with two strands of loose suture consisting of ends of two different pieces of loose suture will be passed through a suitable locking mechanism;

FIG. 44 shows the two sutures loaded in the suture locking mechanism of the anchor body;

FIG. 45 shows the first suture passed through the tissue;

FIG. 46 shows the second suture passed through the tissue at a different location;

FIG. 47 shows a knot tied in the two sutures adjacent to the tissue;

FIG. 48 shows the two sutures being pulled in the indicated direction such that the tissue is drawn toward the anchor body;

Thirteenth Embodiment

Figure 49:
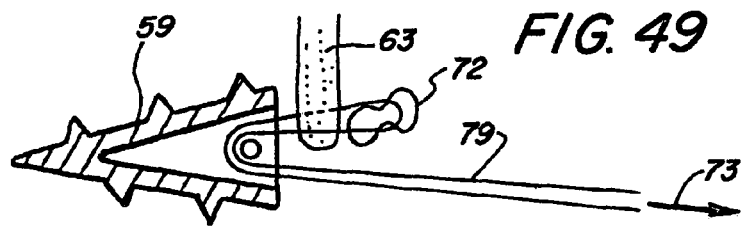

FIG. 49 shows a disk that may be captured by suture in order to prevent the suture from damaging the tissue;

Fourteenth Embodiment

Figure 50:
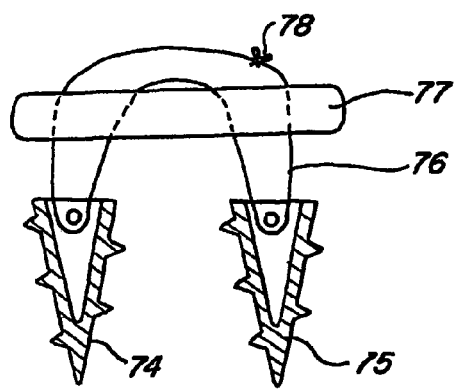

FIG. 50 shows a dual anchor configuration wherein both ends of single piece of loose suture loaded into the locking mechanism of one anchor body are passed through tissue, where one end is passed back through to the other side and loaded in the locking mechanism of the other anchor body (using a suture puller as described earlier), and where the free end of the suture is passed through the tissue again, and where the two free ends are brought together to form a knot;

Fifteenth Embodiment

Figure 52:
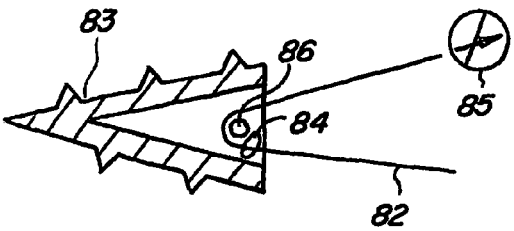
Figure 51:
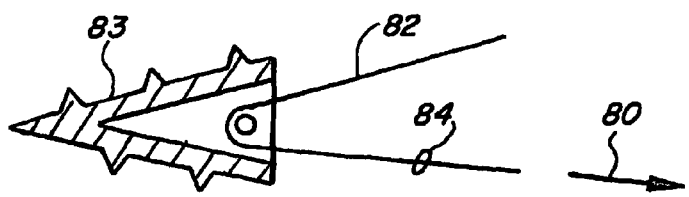

FIGS. 51-52 show another embodiment where suture is locked in place with a locking clip that is pushed down the suture;

FIG. 51 shows the suture having been threaded through the Anchor Body and then around a Retaining Pin, and a locking clip being pushed down toward the anchor body;

FIG. 52 shows the locking clip holding the suture and preventing it from being pulled in the opposite direction via friction, or deformation, or other suitable manner;

Sixteenth Embodiment

Figure 53:
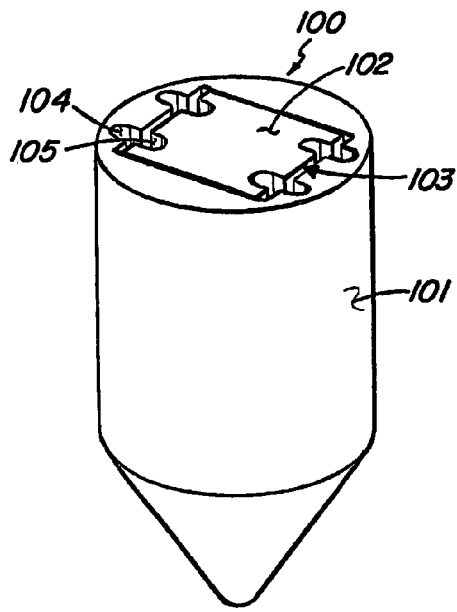
Figure 54:
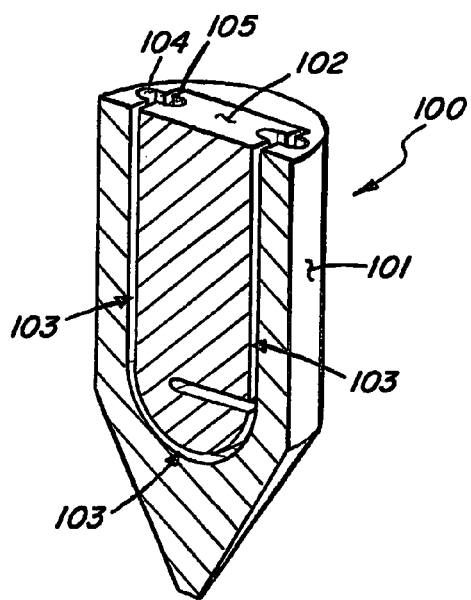
Figure 55:
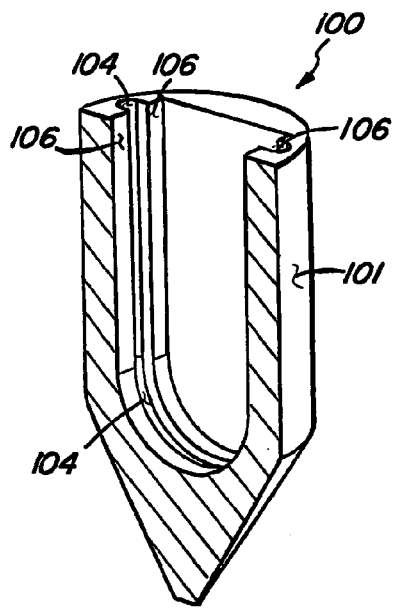
Figure 56:
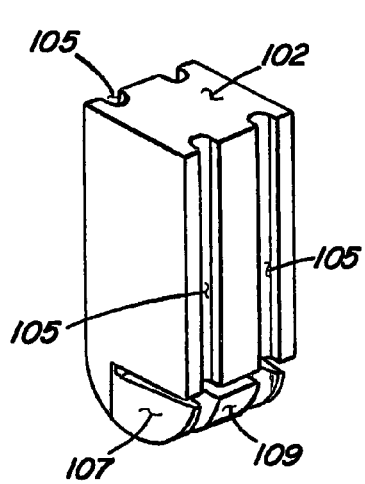
Figure 57:
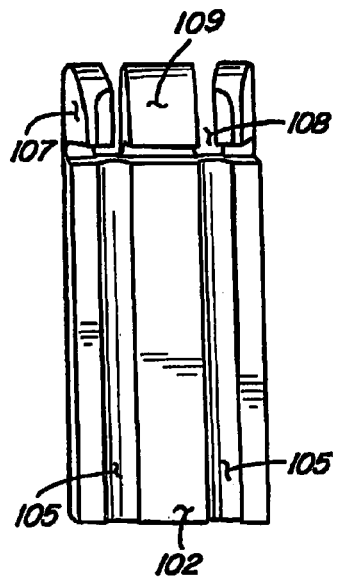
Figure 58:
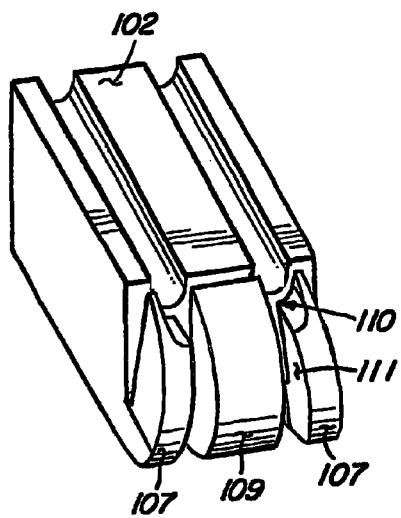
Figure 59:
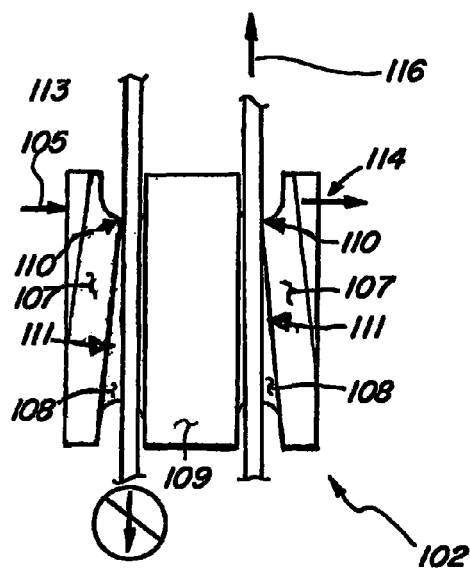
Figure 60:
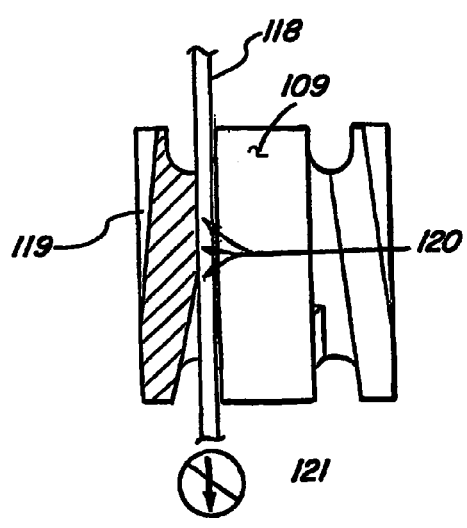
Figure 61:
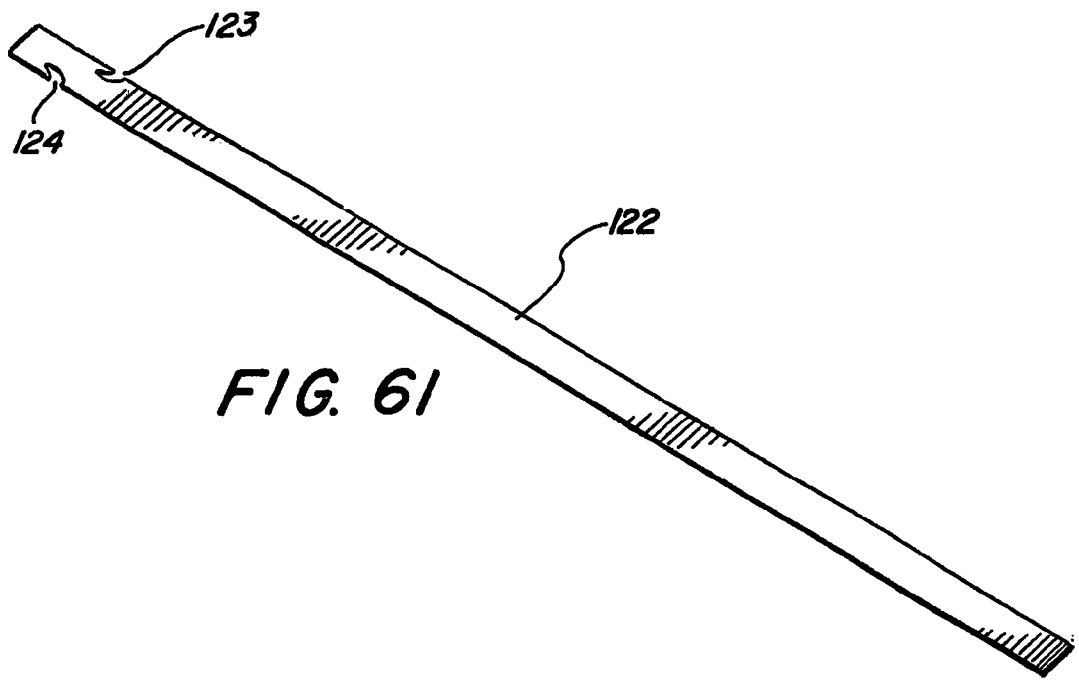
Figure 62:
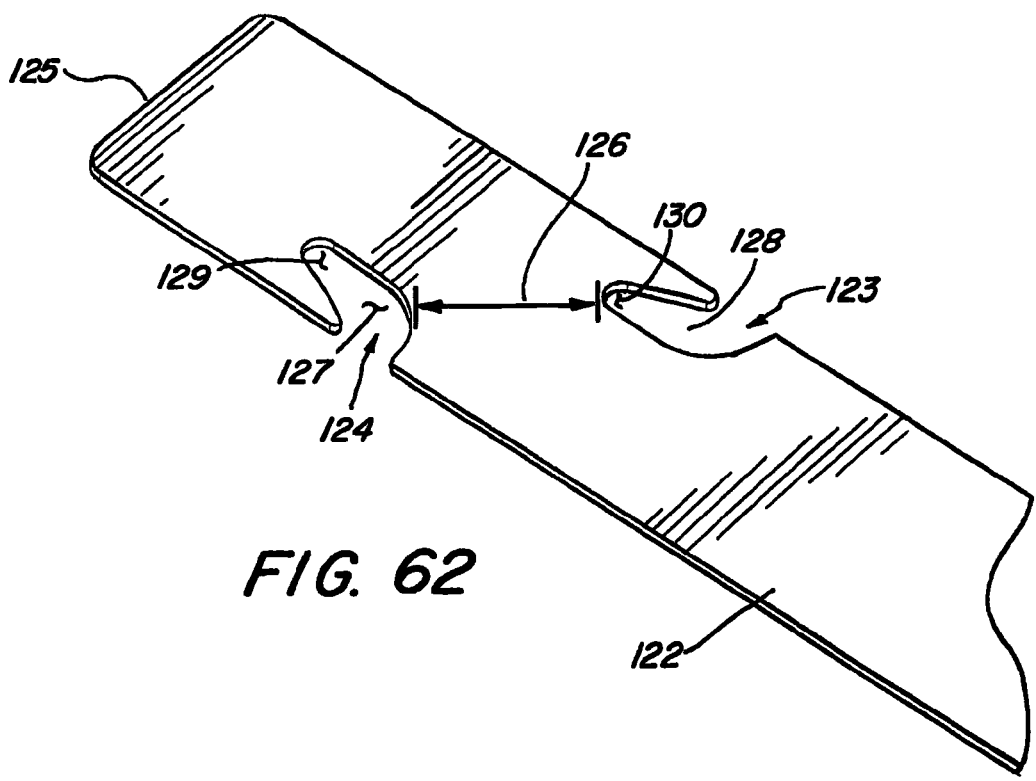
Figure 68:
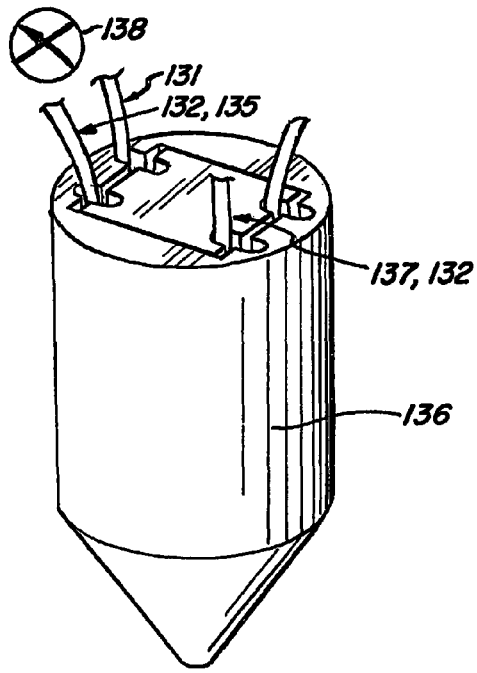

FIGS. 53-68 show a presently preferred embodiment of a suture anchor that includes a suture puller and an integral suture locking mechanism that permits suture to be pulled through the anchor body in one direction using the suture puller, and then after that, substantially permits the suture to be pulled in that same direction but substantially prevents the suture from moving in the other direction (the embodiment show accommodates two sutures, but a suture anchor with only one suture channel would be useful under certain circumstances);

FIG. 53 shows a suture anchor 100 having a body formed from an Insert 102 assembled into a Housing 101;

FIG. 54 is a cross sectional view of the suture anchor of FIG. 53 showing the insert and the housing;

FIG. 55 is a cross sectional view of the suture anchor of FIG. 53 with the insert removed to show only the housing;

FIG. 56 is a perspective view of the insert itself;

FIG. 57 is another view of the Insert from a different angle;

FIG. 58 is another perspective view of the insert, rotated relative to FIGS. 56 and 57;

FIG. 59 shows how the Insert allows suture to slide in one direction and locks it in the other direction;

FIG. 60 shows small directionally biased hooks (optional) that are intended to enhance the suture locking mechanism;

FIG. 61 is an isometric view of a suture puller provided in the form of a pull tab;

FIG. 62 is a close-up view of the tip of the suture puller of FIG. 61;

FIG. 63 shows the suture puller pre-loaded into the suture anchor;

FIG. 64 shows the sutures loaded into suture slots in the suture puller;

FIG. 65 shows that each suture's two tails are being lined up to be pulled into Suture Slots on either side of the suture puller as the suture puller is pulled through the suture anchor;

FIG. 66 shows suture puller having been pulled all the way through the suture anchor such that the two tails of each suture have been threaded through the suture slots in the suture anchor;

FIG. 67 shows one tail of the suture after is has been fully through and clear of the suture anchor, leaving the other tail attached to the suture anchor;

FIG. 68 is a close-up perspective view showing the suture after it has been cut so that a stub is left on one side of the suture anchor and a long tail holding tissue, for instance, is left on the other side.

Seventeenth Embodiment

Figure 69:
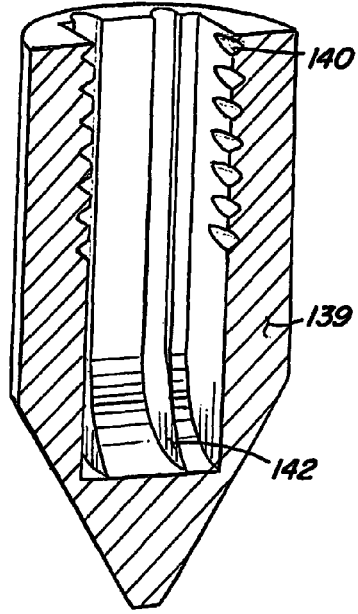
Figure 71:
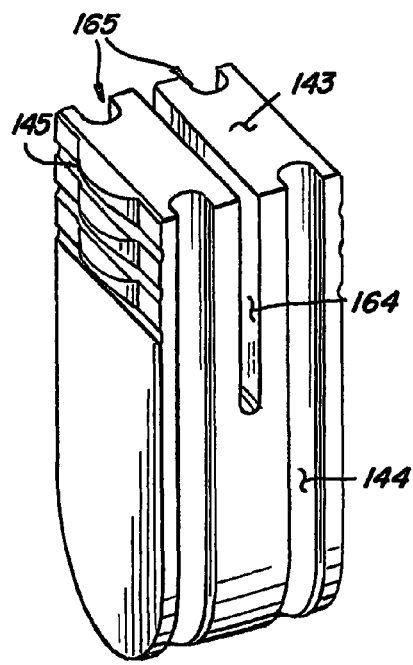
Figure 70:
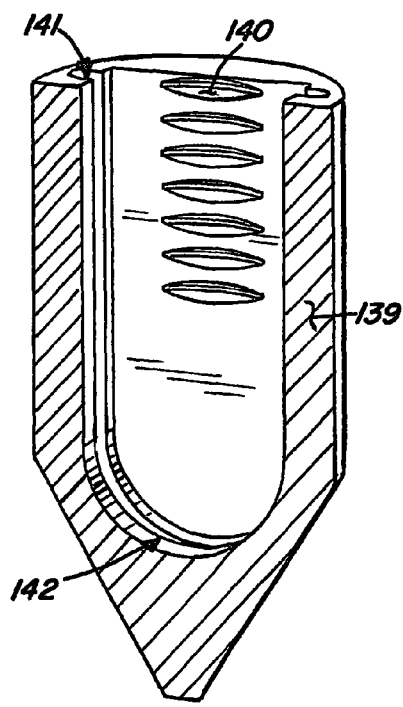
Figures 72, 73:
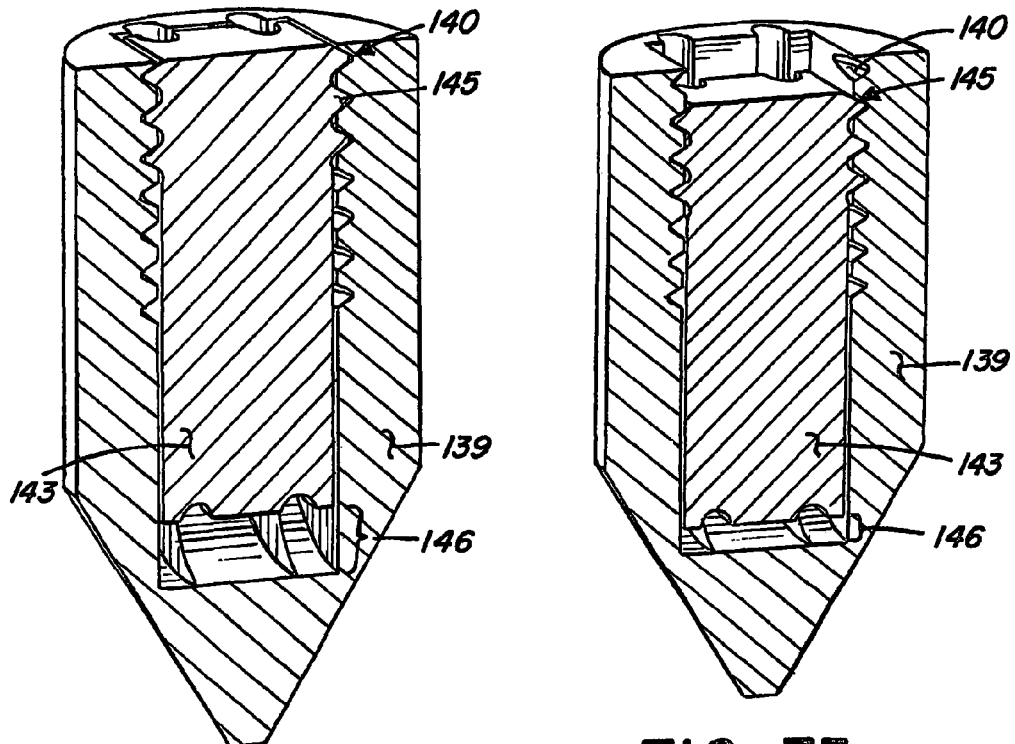
Figure 74:
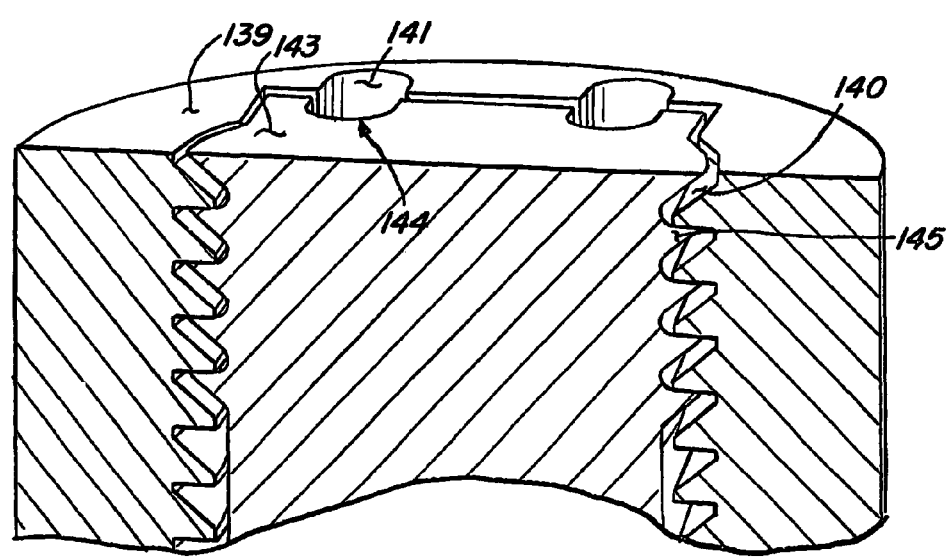

FIGS. 69-74 show an alternative embodiment of a suture anchor that includes a suture puller and an integral suture locking mechanism that includes a ratcheting mechanism for moving the suture locking mechanism between a first open position and a second closed position;

FIG. 69 is a cross sectional view of the housing of the alternative suture anchor;

FIG. 70 is a cross sectional view of the housing taken in a plane that is perpendicular to the plane used in FIG. 69;

FIG. 71 is a perspective view of the mating insert that cooperates with the housing of FIGS. 69-70;

FIG. 72 is a cross sectional view of the insert of FIG. 70 assembled in the housing of FIGS. 69-70;

FIG. 73 shows the insert after it has been moved inward relative to the housing by causing the locking tabs to interface with lower locking notches;

FIG. 74 is a close-up cutaway view of one of many possible configurations for the locking notch and locking tabs;

Eighteenth Embodiment

FIGS. 75-80 show an alternative embodiment that is comparable to the suture anchor embodiment of FIGS. 69-74 except that the ratcheting mechanism has been changed to an interface between the centerline of the insert and a cross pin that has been placed through the center of the housing;

FIG. 75 is a perspective view of the modified insert provided with a cross pin channel;

FIG. 76 shows the cross pin;

FIG. 77 shows the cross pin assembled to the housing with the insert missing;

FIG. 78 is a cross sectional view of the cross pin, insert, and housing after they have been assembled;

FIG. 79 is a cross sectional view showing the suture anchor in a suture unlocked position with a relatively large gap below the insert;

FIG. 80 is a cross sectional view showing the suture anchor in a suture locked position with a smaller gap below the insert;

Nineteenth Embodiment

FIGS. 81-84 show an another embodiment of a suture anchor having a particular locking mechanism that is formed from a pivoting member (here a cam member) that is biased against an inner wall of the suture anchor;

FIG. 81 is a perspective view of the cam member;

FIG. 82 is an end view of the cam member;

FIG. 83 is a cross sectional view of the cam member assembled into the housing and having a cam actuation wire attached thereto;

FIG. 84 is a cross sectional view of the suture anchor wherein the cam member has been rotated such that its cam surface is pinching the suture (not shown) against the inner housing wall and such that a locking knob on the cam member has clicked into a into a mating notch on the housing;

Twentieth Embodiment

Figure 85:
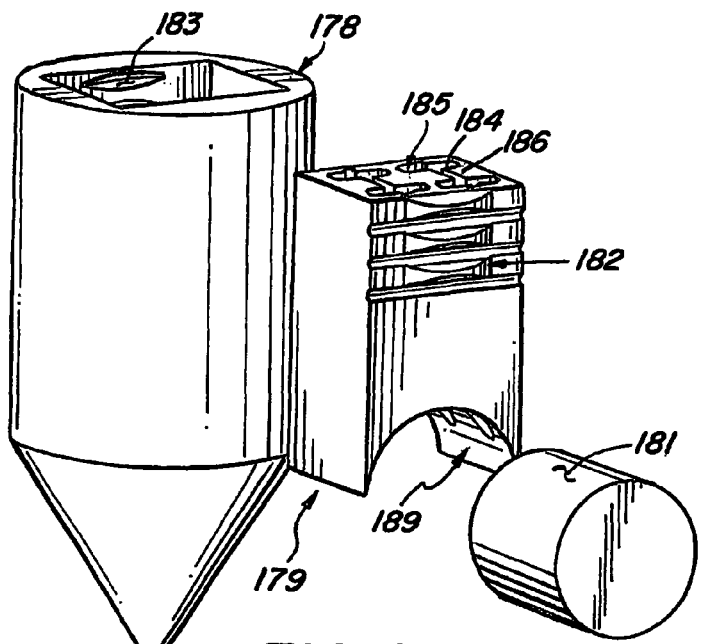
Figure 86:
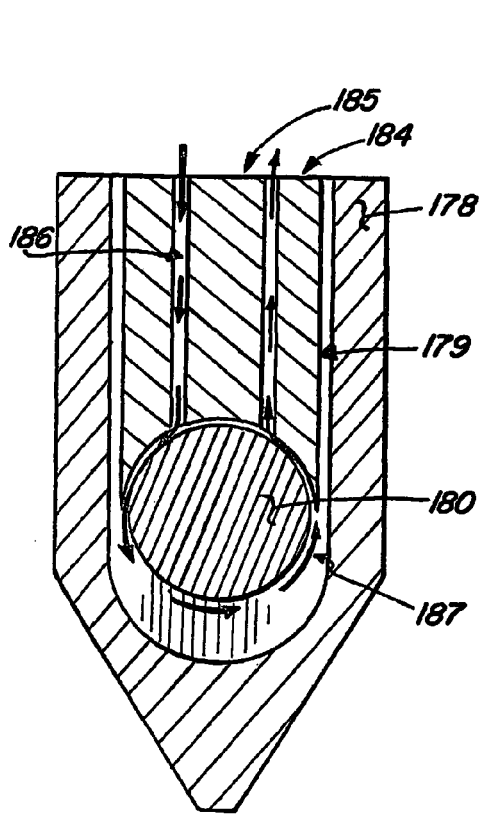
Figure 87:
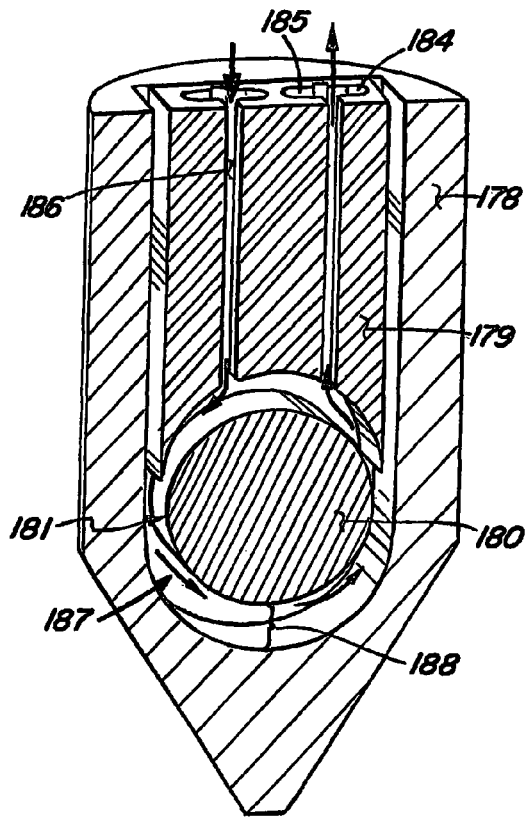
Figure 88:
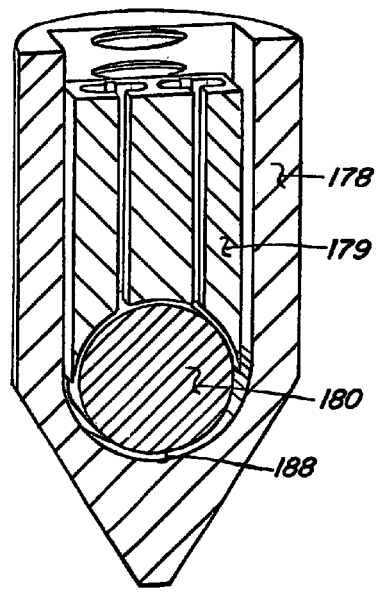

FIGS. 85-88 show an another embodiment of a suture anchor having a particular locking mechanism that is formed from a one-part housing, an insert, and a locking pin (that latter two might be regarded as a two-part insert) that provide a circuitous path for enhanced locking;

FIG. 85 is an exploded view of the three parts;

FIG. 86 shows the general path 187 of the pull-tab and the suture;

FIG. 87 shows the insert in the up position such that the locking pin is in a spacious condition and the suture may slide freely through the gap illustrated by the arrows;

FIG. 88 shows the insert after it has been pushed in to the housing and is pushing the locking pin into a position that creates a very small gap thus holding the suture in place;

Twenty-First Embodiment

Figure 89A:
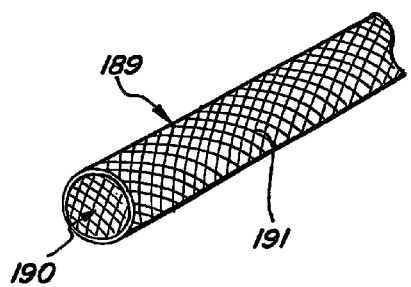
Figure 89B:
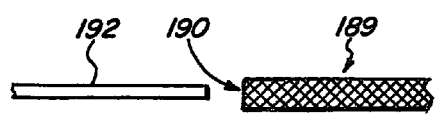
Figure 89C:
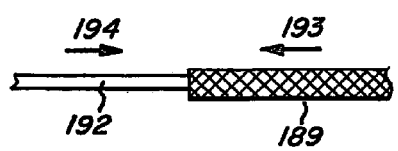
Figure 89D:
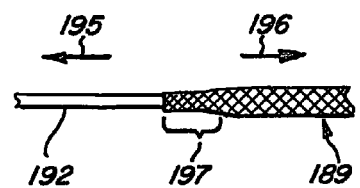

FIGS. 89A-89D show an alternative suture puller formed as a trap pull tab where at least the distal end is made of a woven material such that the device acts like a finger trap when grabbing the suture and pulling it through the anchor;

FIG. 89A shows the end of the trap pull tab;

FIG. 89B shows the suture is about to be placed in the opening of the trap pull tab;

FIG. 89C shows the motion of sliding the suture into the trap pull tab;

FIG. 89D shows that when the motion is reversed, the trap pull tab collapses around the suture for pulling it through the suture locking mechanism of a suture anchor according to an embodiment of the present invention;

Twenty-Second Embodiment

Figure 90:
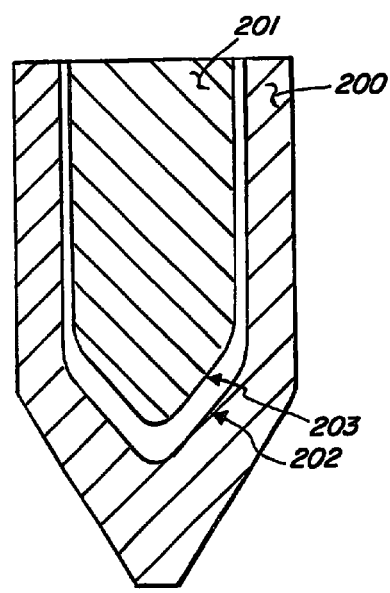

FIG. 90 shows a cross sectional view of a housing and insert that have been modified slightly such that their distal ends are substantially V-shaped rather than U-shaped.

DESCRIPTION OF PREFERRED EMBODIMENTS

In accordance with at least one embodiment of the present invention, an anchor is presented with an elongated suture puller (aka a shuttle) to thread suture through the locking mechanism located in the anchor's center. The anchor in this embodiment as with all the presented designs can be embodied in an anchor having an anchor body with any suitable means for anchoring the anchor body to the bone of a patient. The anchoring means includes, for example, a push-in, screw-in, eared, or other styles of implant. FIG. 1 shows a screw-in style anchor as an example.

A strand of Suture 1 is affixed to the Anchor Body 2 at an Affixation Point 5. The Affixation Point 5 is shown as a method of how the suture can be attached to the anchor. A Locking Mechanism 4 is shown schematically in the Anchor Body 2 that has a bias to allow the Suture 1 or elongated suture puller 3 having first and second lengths extending from the anchor body to slide in one direction but not the other. For this example the Anchor Body 2 can be considered as in bone. The elongated suture puller 3 is shown threaded in the Anchor Body 2 around the Locking Mechanism 4.

Figure 2:
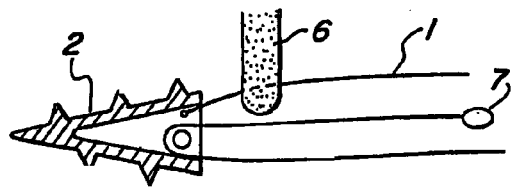
Figure 3:
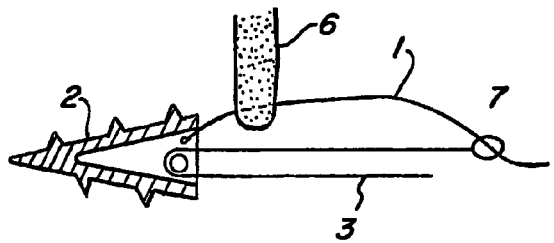
Figure 4:
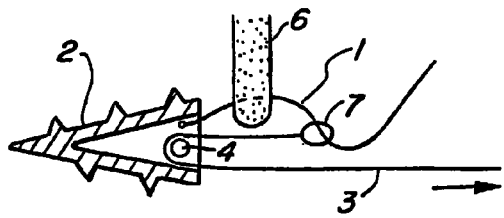
Figure 5:
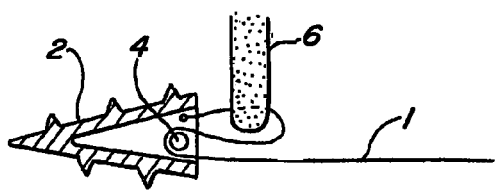
Figure 6:
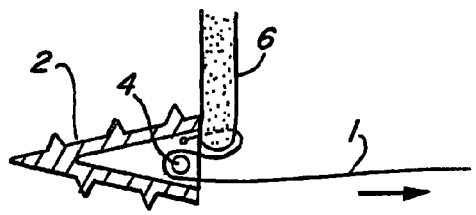
Figure 7:
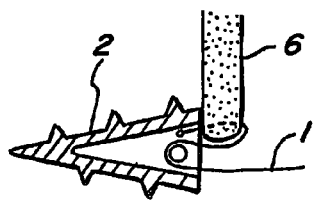

In FIG. 2 the Suture 1 has been passed through a piece of Tissue 6. The Suture 1 is then threaded through a suitable means for engaging the suture such as, but not limited to, the Shuttle Loop 7 shown in FIG. 3. The elongated suture puller 3 is then pulled in a direction allowed by the Locking Mechanism 4 so that the Suture 1 is pulled (see FIG. 4) until the Suture 1 is threaded in the Anchor Body 2 around the Locking Mechanism 4 as shown in FIG. 5.

The Suture 1 can then be pulled to the proper tension so that the Tissue 6 is pulled toward the Anchor Body 2 and against the bone for proper healing. The Locking Mechanism 4 restricts movement of the Suture 1 in the opposite direction so the tension on the Tissue 6 does not decrease (see FIG. 6). To complete the process the Suture 1 is trimmed as in FIG. 7 to the desired length.

This same example could be slightly modified such that the Suture 1 is passed through Tissue 6 before the Anchor Body 2 is placed in bone. This allows the Suture 1 to be threaded into the Anchor Body 2 outside of the body. The Anchor Body 2 can then be easily placed in the bone and the Suture 1 tightened to the desired position.

The following section describes some possible locking mechanisms. FIGS. 8 and 9 are a top and side cut-away view respectively of Locking Mechanism 4 in an Anchor Body 2. The Locking Mechanism 4 is made of the Spring 8, the Locking Paddle 9, and the Connecting Member 10. In this configuration the Connecting Member 10 holds the Locking Mechanism 4 in place relative to the Anchor Body 2. The Spring 8 is pushed against the Inner Wall 11 of the Anchor Body 2 so that a resulting force translates to the Locking Paddle 9 pushing it against the opposite Inner Wall 12 of the Anchor Body 2.

The same Locking Mechanism 4 is shown in FIGS. 10 and 11 except Suture 13 has been added. The Suture 13 is threaded into the Anchor Body 2 between the Inner Wall 12 and the Locking Paddle 9, through the Spring 8 and out the other side of the Anchor Body 2. When the Suture 13 on the side of the Spring 8 is pulled as shown 14 it tends to rotate the Locking Paddle 9 away from adjacent Wall 12, shown here as counterclockwise so that a gap is created between the Locking Paddle 9 and the Inner Wall 12 allowing the Suture 13 to slide freely 15.

In FIGS. 12 and 13 everything is the same except the direction of the Suture 13 has changed. The action of the Suture 13 being pulled in the opposite direction 16 will cause the Locking Paddle 9 to rotate toward the adjacent Wall 12, shown here as clockwise. With the addition of the transmitted force from the Spring 8/Inner Wall 11 interaction the Locking Paddle 9 will tend to push against the Inner Wall 12 and pinch the Suture 13) so as to minimize movement 17. The harder the Suture 13 is pulled 16 the greater the pinching force between the Locking Paddle 9 and the Inner Wall 12 further hindering any suture movement 17. With the Suture 13 at rest the Locking Paddle 9 will be biased to pinch the Suture 13 against the Inner Wall 12 from the force generated by the Spring 8/Inner Wall 11 interaction.

FIGS. 14 and 15 represent a variation of a Locking Mechanism 4. The Locking Paddle 19 is attached to the Anchor Body 2 via a Torsional Spring 18. The Torsional Spring 18 is attached firmly to the Anchor Body 2 so that Locking Paddle 19 is in close proximity to the Inner Wall 12. As in the previous example if the Suture 13 is pulled in one direction the Locking Paddle moves away from adjacent Wall 12, shown here as counterclockwise creating a larger gap between the Locking Paddle 19 and the Inner Wall 12 so that the Suture can move freely 21. If the Suture 13 is pulled in the opposite direction the Locking Paddle is rotated toward the adjacent Wall 12, shown here as clockwise. This is in addition to the Torsional Spring 18 biasing the Locking Paddle 19 toward the Inner wall 12. With these two actions the Suture 13 tends to be pinched between the Locking Paddle 19 and the Inner Wall 12 hindering any suture movement 22.

Note that optional surface finishes can be applied to the Locking Paddle 19 to better interact with the Suture 13. Shown are Teeth 20 but general material roughness or other surface finishes can be used.

Though the cross section of Torsional Spring 18 shown in FIG. 15 is round it can be shaped in a variety of other ways. Some examples are given in FIG. 16. The cross section also does not need to be consistent along its length.

In accordance with an embodiment one end of the suture may need to be attached to the anchor in some fashion. FIGS. 17 and 18 are a top and cut-away side view of an Anchor Body 2 with a Cross Pin 23 captured or attached. A void has been made in the Cross Pin 23 that receives the Suture 13. The Suture 13 can be attached to the Cross Pin 23 in a variety of ways including but not limited to mechanical (e.g., crimping, friction) or chemical (e.g., adhesive, melting) methods.

A variation of this design is shown in FIGS. 19A, 19B, and 20. The Suture 13 comes out both ends of the Cross Pin 23 so that two strands are ready for passing through tissue. An optional Notch 24 has been made in the Anchor Body 2 to act as a relief for the Suture 13 to make the transition from the axis of the Cross Pin 23 to roughly the axis of the Anchor Body 2). The Suture 13 can be fashioned in the Cross Pin 23 to slide or be permanently attached. FIG. 19B shows a variation of two pieces of suture (25 and 26) in the Cross Pin 23.

FIG. 21 shows the Suture 13 placed directly in the wall of the Anchor Body 2 This can be done in many ways and is not limited to mechanical coupling, chemical coupling, and over molding. More than one suture can be attached this way.

FIGS. 22 through 27 present a different design for clamping suture in an anchor. A Suture 27 is attached to an Anchor Body 28 at a Fixation Point 29 as shown in FIG. 22. The Anchor Clip 30 is separate from the Anchor Body 28 initially. The Suture 27 is passed through the Tissue 31 in FIG. 23. The Anchor Clip 30 is slid down the Suture 27 and attached to the Anchor Body 28 as shown in FIGS. 24 and 25.

FIG. 26 shows the Suture 27 being pulled in a direction 32 such that the Suture 27 weaves through the Anchor Clip 30 pulling the Tissue 31 toward the Anchor Body 28. Once the desired tightness is reached of the Suture 27 and the Tissue 31 the Suture 27 can be trimmed to the appropriate length as in FIG. 27.

It should be noted that many of the details described in FIGS. 8 through 21 also apply to the previous concept. One difference is the Anchor Clip 40. The following figures provide details for this clip. FIG. 28 shows 3 views of the same anchor clip concept. The Connecting Member 35, which attaches to the anchor, is the vertex for the Locking Paddle 33 and the Spring 34. The Locking Paddle 33 has an included Notch 36 to act as a guide for suture. The height of the Notch 36 is less than the diameter of the suture to be used to that it can act to pinch the suture between the Locking Paddle 33 and the Inner Wall 39 of the anchor. The Spring 34 includes a Void 37 that acts to capture and direct the suture inside the anchor. The void 37 is shown as a circle but can be many different shapes and/or open to a side.

In FIG. 29 the Suture 40 has been threaded against the Notch 36 and through the Void 37. The Anchor Clip 43 has been slid down the Suture 40 and placed inside the anchor so the Connecting Member 35 is attached to the anchor, the Spring 34 is pressed against one Inner Wall 38 pushing the Locking Paddle against the other Inner Wall 39. This action tends to pinch the Suture 40 between the Notch 36 of the Locking Paddle 33 and the Inner Wall 39. As with the earlier described idea if the Suture is pulled in one direction 42 the pinch becomes greater and the Suture 40 cannot move. But if the Suture 40 is moved in the other direction 41 the Locking Paddle 33 rotates slightly loosening the pinch and allowing the Suture 40 to slide.

A variation of this concept is described in FIGS. 30 to 32. In place of the Notch 36 on the Locking Paddle 33 a Pinching Void 46 is used. When a Force 48 is applied to the Collapsible Wall 47 the Pinching Void 46 becomes misshapen and pinches the Suture 40 to hold it in place. FIG. 33 describes how the Suture 40 can slide when pulled in one direction 48 and locks in place when pulled in the other direction 49.

FIGS. 34 to 36 describe a tool that can be used to release the lock so suture can be slid in either direction. FIG. 34 shows the direction 50 in which the Suture 40 is locked and cannot move. Only the distal end of the Release Tool 51 is shown. A handle is attached that allows the doctor to use it in the constraints dictated by surgery. The Release Tool 51 includes two distal Arms (52 and 53) that define a V-Notch 55 A radius on the inner distal portion of the arm or Lead-in 54 is included on each Arm (52 and 53). In use, the Release Tool 51 is placed over the clip so that the Arms (52 and 53) collapse the Locking Paddle 57 and Spring 56 together. This action releases the pinch force between the Locking Paddle 57 and the Inner Wall 58 so the Suture 40 can slide in a direction 58 that it previously could not.

FIGS. 37 through 42 describe an alternative embodiment where the suture is initially not connected to the anchor. An Anchor Body 59 is loaded with an alternative embodiment of an elongated suture puller 60, which is wrapped around a Locking Mechanism 61. The elongated suture puller 60 includes a means for engaging suture formed from a Threading Loop 64. Suture 62 with a Suture Loop 65 and Tissue 63 are also presented.

First the Suture 62 is passed through the Tissue 63 as shown in FIG. 38. The passed end of the Suture 62 is threaded through the Suture Loop 65 and the passed end is pulled taut so the Suture 62 is tight against the Tissue 63. The free end of the Suture 62 is now passed through the Threading Loop 64 as described in FIG. 40. A first length of the elongated suture puller 60 is pulled in a direction 67 so that it slides around the Locking Mechanism 61 pulling the Suture 62 captured by the Threading Loop 64 with it.

In FIG. 41 the elongated suture puller 60 has been pulled all of the way through the Anchor Body 59 and has threaded the Suture 62 around the Locking Mechanism 61. The Suture 62 can be pulled in a direction 66 so that the Tissue 63 is drawn towards the Anchor Body 2. As previously described the Suture 62 can be trimmed once the tissue is adequately approximated. This method can also be done with two or more sutures connected to a single anchor after completion.

An alternative method is shown in FIGS. 43A and 43B where a loose piece of Suture 67 has been attached to Tissue 63 with a Mattress Stitch 68. A variety of stitches could be used in this situation but the Mattress Stitch 68 is used as an example. The two passed arms of the Suture 67 can now be threaded through the Anchor Body 59 as depicted in FIG. 40.

Another alternative method is shown in FIGS. 44 to 48. Two Sutures (69 and 70) are loaded in the Anchor Body 59. The Sutures 69 and 70 are passed through the Tissue 63 one at a time in different areas. A Knot 71 is tied in the passed Sutures (69 and 70) and is then pulled in a direction 73 that tightens the Tissue 63 toward the Anchor Body 59.

FIG. 49 shows a variation with a Disk 72 looped in the Suture 79 such that when the Suture 79 is tightened against the Tissue 63 the Disk 72 acts as a barrier to keep the Suture 79 from damaging the Tissue 63. The two strands of suture can also exit from the same hole so that the Disk 72 keeps the Suture 79 from going back through the hole when pulled in the direction 73.

FIG. 50 shows the final configuration of a method where both ends of the Suture 76 loaded in Anchor Body #1 74 were passed through the Tissue 77. One end was passed back through to the other side and loaded in Anchor Body #2 75 as described earlier. This free end of suture is passed again through the Tissue 77. The two ends of the Suture 76 are brought together to form a Knot 78.

It should be noted that these sutures could be colored differently to aid in suture management. Also the means for anchoring associated with the anchor bodies of the anchors can be the push-type, the screw-type, or the arm-type or any other style of tissue fixation device that holds adequately and can contain the above-described mechanisms. The anchors are shown with anchor bodies in cylindrical form but they can have an oval, rectangular, triangular or any other appropriately shaped cross section.

FIGS. 51 and 52 describe an additional embodiment for locking the Suture 82 in the Anchor Body 83. The Suture 82 is threaded through the Anchor Body 83, around the Retaining Pin 86. The Suture 82 is also threaded through or joined with the Locking Clip 84. When the Suture 82 has been pulled 80 to the desired tautness the Locking Clip 84 is slid down the Suture 82 until it clips into place in or on the Anchor Body 83. The Locking Clip 84 can hold the suture in a frictional manner or be deformed around the Suture 82 or utilize some other mechanism so that the Suture 82 cannot be pulled in the opposite direction 85.

The remainder of this disclosure presents other embodiments of the present invention that are comparable to the embodiments of FIGS. 1-7 or 37-42 in that an anchor is presented with an elongated suture puller that is preloaded in the suture anchor in order to pull or thread suture through the locking mechanism located in the anchor's center. The suture anchor used in these embodiments, as with all the above designs, can be a push-in, screw-in, eared, or other suitable style of bone fixation implant.

FIGS. 53-68 show an embodiment where the elongated suture puller is comprised of a Pull Tab 122 (best shown in FIGS. 61 and 63). Starting with just the anchor body, FIG. 53 shows a suture anchor 100 having a body formed from an Insert 102 assembled into a Housing 101. The insert 102 can be secured to the housing 101 via any suitable means such as a mechanical interconnect, a press-in fit, a weld, adhesive, etc. There are four sets of Outer Suture Channels 104 and Inner Suture Channels 105 and two Pull Tab Channels 103. FIG. 54 is a cross sectional view of the previous figure. It shows how the Pull Tab Channel 103 is actually continuous between the two openings at the top.

In FIG. 55 the insert 102 has been removed leaving a cross sectional view of the Housing 101. The Outer Suture Channel 104 is exposed showing that it is continuous between the two end points at the top of the component. The Outer Pull Tab Channel Wall 106 is also shown.

The Insert 102 is shown by itself in FIG. 56. In this view the Inner Suture Channels 105 go along the length of the Insert 102. One of two Locking Tabs 107 is shown. FIG. 57 is another view of the Insert from a different angle. Again, the Inner Suture Channels 105 and the Locking Tabs 107 can be seen. The Middle Post 109 is the stationary piece between the two Locking Tabs 107. The Suture Gap 108 separates the Locking Tab 107 from the Middle Post 109. FIG. 58 is another rotated view of the Insert 102, which is meant to showcase the Locking Point 110 at the end of the Locking Tab 107. The Locking Point 110 is shown as the intersection of three curves but could be geometrically altered to be a rough surface or be combined with a modified Inside Tab Surface 111 to perform suture-locking duties.

The action of the Insert 102 to allow suture to slide in one direction and to lock it in the other is represented in FIG. 59. When the Suture 112 is pulled up 116 (directionally as shown on the figure) it slides through the Suture Gap 108 and past the Locking Point 110. This is because the Locking Tab 107 can flex to the right 114 to allow relatively free movement of the Suture 112. When the Suture 113 is pulled in the opposite direction, down 117, the Suture 113 is restrained from moving by the spring force of the Locking Tab with a directional component 115 that biases the Locking Point 110 towards the Middle Post 109. This acts to frictionally hold the suture in place. The geometries of the Locking Point 110 and the Inner Tab Surface 111 can be modified to enhance this frictional interaction or to make it so the closing force between the Locking Tab 107 and the Middle Post 109 is increased with additional pull force in the downward direction 117. This could be done in many ways such as creating small directionally biased hooks on the Inner Tab Surface 111. FIG. 60 shows a possible method for this by modifying the Locking Tab 119 to include small Hooks 120. When the Suture 118 is pulled in the downward direction 121, the Locking Tab 119 pushes against the Suture 118 so that it presses the latter against the Middle Post 109 so that the Hooks 120 tend to 'grab' on to the Suture 118 holding it in place. As drawn the Hooks 120 face slightly upwards so that they will grab the Suture 118 in the downward direction 121, but allow the Suture 118 to slide more freely when pulled in the opposite direction.

FIG. 61 is an isometric view of the elongated suture puller provided here as a Pull Tab 122. This component is used to thread sutures through the implant. It tends to be a long, thin ribbon with a cross section that allows it to bend in one axis relatively easy compared a perpendicular axis. A close-up of the tip at the end of one length thereof is shown in FIG. 62. A first proximal length thereof (lower right) is pulled by the surgeon in use. A second opposite distal length thereof (upper left) contains suitable means for engaging suture such as a slot.

Two Suture Slots 127 and 128 can either be in line (same distance from the distal end 125) or offset as shown to increase the web thickness 126 in order to improve strength. A Suture Slot Opening 123 and 124 allows suture to be easily loaded in to the Suture Slot 127 and 128. As the Pull Tab 122 is pulled away from the distal end 125 the suture will tend to slide into the tapered slot 129 and 130 and lock into place.

FIGS. 63 to 67 describe how suture is loaded and locked in place. FIG. 63 shows the Pull Tab 122 pre-loaded into the implant represented by the assembly of the Insert 102 in the Housing 101. In FIG. 64, Sutures 131 and 132 have been loaded into Suture Slots 127 and 128 of the Pull Tab 122. The Sutures 131 and 132 could also be two ends of the same suture. For the rest of the description the action of only one Suture 132 will be described but a similar action will exist for Suture 131.

As the Pull Tab 122 is pulled in the direction shown 133, the distal end of the Pull Tab 125 moves towards the Implant 136, pulling the Suture 132. The suture's two tails 134 and 135 are being lined up to be pulled into Suture Slots 104 and 105. This is shown in FIG. 65.

In FIG. 66, the Pull Tab 122 has been pulled all the way through the Implant 136 so that the two Tails 134 and 135 have been threaded through Suture Slots 104 and 105 respectively. In FIG. 67, the Tail 134 has been pulled fully through the Implant 136 leaving Tail 135 attached to the Implant 136. In FIG. 68, the Suture 132 has been cut so that a Stub 137 is left on one side of the Implant 136 and a long Tail 135 holding tissue, for instance, is left on the other side. Based on the mechanisms within the Implant 136 described in FIGS. 54-60, the Sutures 131 and 132 cannot move in the retro direction 138.

In the subsequent drawings related to other embodiments, the suture and the elongated suture puller have been omitted for clarity. However, it should be assumed that they are included and serve the same general purpose as in the previously presented embodiments.

FIGS. 69 through 74 illustrate an alternative structure for holding suture. The basic idea is the same as previously discussed, but instead of a clamping mechanism included in the insert the suture is held between the insert and the housing by changing the position of the two components relative to each other. Thus, this is a two-state device having an open state where the suture can move in either direction and a closed state where the suture is compressed and locked in place and prevented from moving in either direction.

In FIG. 69 a cross sectional view of the housing 139 is presented. This view exposes the outer suture channel 141 which differs from those previously discussed in that the depth tapers lower near the bottom 142 of the housing 139. This will act to enhance interference force on the suture in the suture-hold position. One-half of each locking notch 140 can also be seen. A cross sectional view from a perpendicular plane is shown in FIG. 70. A full view of one set of the locking notches 140 is shown along with a different view of the tapering outer suture channel 142.

The mating insert 143 is represented in FIG. 71. The inner suture channels 144 are similar to those previously discussed except the channel follows the contour around the shape and the spring locking mechanism is removed. Locking tabs 145 have been added that will be mating with the locking notches in the assembly and a relief channel 164 aids the flexibility of the two insert posts 165.

FIG. 72 is a cross sectional view of the insert 143 assembled in the housing 146. The relative position of the two parts allows for a gap 146 such that the suture can slide freely between them. The interaction of the locking notches 140 and the locking tabs 145 can also be seen. The optional relief channel 164 is not shown. In FIG. 73, the insert 143 has been moved relative to the housing 139 by moving the locking tabs 145 to interface with lower locking notches 140. This leaves a smaller gap 147 which will tend to compress the suture threaded between the insert 143 and housing 139 and hold it in place. One of many possible locking notch 140/locking tab 145 configurations is shown in the close-up view of FIG. 74.

Another suture locking variation is presented in FIGS. 75 to 80. Here, the positional locking mechanism has been changed to the centerline of the insert and a cross pin has been placed through the center of the housing.

The modified insert 148 is shown in FIG. 75 with similar inner suture channels 149. The locking channel 165 consists of several locking levels 166, the cross pin channel 153, and the relief channel 154. The locking levels consist of a taper 152 that rides along the cross pin during the motion to lock suture, a insert flat 151 which locks against the flat surface of the cross pin to keep the insert from backing out of the housing, and a radius 150 that attaches the two features and may be a resultant of the manufacturing process. The cross pin channel 153 is an optional feature that can help the assembly by allowing a place for cross pin insertion with the insert already in the housing. The relief channel 154, which is also optional, can be varied in length to change the ability for spreading movement for a given force.

The cross pin 155 is shown in FIG. 76. This component consists of two rounded ends 156 and a triangular cross-sectioned center with three faces 157, 167 and 168. In FIG. 77 the cross pin 155 is assembled to the housing 158 with the insert missing. The rounded ends 156 have been placed in the housing holes 159.

In the cross sectional view of FIG. 78 the cross pin 155, insert 148 and housing 158 have been assembled. The functions of the cross pin faces 160 are to act as a wedge to push the taper 152 apart so the cross pin can advance to the next locking level 166. The cross pin flat 161 acts to push against the insert flat 151 so that the insert 148 will not back out of the housing 158.

FIGS. 79 and 80 show this described assembly in the suture unlocked position (FIG. 79) with a relatively large gap 162 and the suture locked position (FIG. 80) with a smaller gap 163. In the two figures it can be seen that the cross pin 155 has changed from one locking level 166 to another.

As with all the ideas presented there are numerous possible configurations for the presented geometries such as a non-triangular cross pin or locking tab/locking notch fits, etc.

Another variation of these suture anchor ideas is presented in FIGS. 81 to 84. In this system the insert is modified to have a cam device at its bottom, or is replaced altogether with a cam device, which may or may not be attached to the housing. The following example shows the cam pinned to the housing.

Detailed views of the cam 167 are shown in FIGS. 81 and 82. This component has a rotation hole 169, which connects it to the housing via a pin. This hole is off the center axis of face 172. If the cam 167 is not attached to the housing the rotation hole 169 is optional. The cam hole 168 is off axis of the rotation hole so that if a wire or suture is attached at the cam hole 168 the wire can be pulled to rotate the cam 168 about the rotation hole 169 or some other point if not attached to the housing. The cam surface 170 acts as a curved plate to compress the suture against the inside surface of the housing thus holding the suture (not shown) in place. The locking knob 171 locks the cam 167 at the correct rotation or placement so that the suture cannot slide.

FIG. 83 is a cross sectional view of the cam 167 assembled into the housing 173 and pinned at the rotation hole 169. The housing 173 is similar to the designs discussed earlier. At this point the suture (not shown) can be pulled around the cam 167 in a counterclockwise direction. A cam actuation wire 175 is shown but not yet in use. In FIG. 84 it is assumed that the suture (not shown) is fully threaded and in its proper place.

The cam actuation wire 175 is pulled 176 for rotating the cam 167 about the rotation hole 169. This continues until the cam surface 170 is pinching the suture (not shown) against the inner housing wall 177 and the locking knob 171 locks into a mating notch (not shown). This will hold the cam 167 in place and keep the suture from sliding.

Another variation is presented in FIGS. 85 to 88. In this embodiment, the suture is placed through a more circuitous path thus increasing the frictional surface area for holding the suture. Numerous possible approaches exist, but the one presented here differs from the previous methods in that the insert is split into two parts so that the pull tab and suture must go thru a major portion of a circumference that will act as the frictional surface.

FIG. 85 shows an exploded view of the three parts. The housing 178 is similar with locking notches 183. The insert 179 now contains the inner suture channels 185, the outer suture channels 184, and the pull-tab channels 186. The locking tabs 182 exist as before. The bottom of the insert 179 has been removed creating the insert suture surface 189. This will act as a face to hold the suture in place when forced against the locking pin suture surface 181. As mentioned the locking pin 180 has a suture surface 181 that will act as one half of the 'sandwich' holding the suture in place when locked in place.

FIG. 86 shows the general path 187 of the pull-tab and the suture. The pull-tab (not shown) will travel along the pull-tab channel 186 and the suture (also not shown) will follow the inner suture channel 185 and the outer suture channel 184.

In FIG. 87 the locking pin 180 is not locked since the insert 179 is still in the up position allowing the suture to slide freely through the gap 188. In FIG. 88 the insert 179 has been pushed in to the housing 178 pushing the locking pin 180 into a position that creates a very small gap 188 thus holding the suture in place.

FIGS. 89A to 89D describe a variation of the suture pull tab (see e.g. FIG. 61) formed as a trap pull tab where at least the distal end is made of a woven material such that the device acts like a finger trap when grabbing the suture and pulling it through the anchor.

In FIG. 89A the end of the trap pull tab 189 is shown. An opening 190 will be used as an insertion point for suture. The woven mesh 191 can be made of metal wire, plastic or any other material that will act to collapse the diameter when the tension is placed along its long axis.

In FIG. 89B the suture 192 is about to be placed in the opening 190 of the trap pull tab 189. The suture 192 is slipped into the trap pull tab 189 with the motion 194 and 193 shown in FIG. 89C. When the motion is then reversed 195 and 196, the trap pull tab 189 collapses 197 around the suture 192 holding the two components together as shown in FIG. 89D. This allows the user to now thread the suture 192 through the anchor by pulling on the already loaded trap pull tab 189.

The two components can be separated by compressing the trap pull tab 189 which will increase the diameter (not shown) allowing the suture 192 to slide out of the opening 190.

FIG. 90 shows a cross sectional view of a housing 200 and insert 201 that have been modified slightly near their distal ends. Instead of a "U" shaped bottom the insert distal end 203 and the housing cavity distal end 202 are closer to a "V" shape with curved edges.

Although the invention has been discussed with reference to specific embodiments, it will be apparent that the concept can be otherwise embodied to achieve the advantages discussed.

The invention claimed is:

1. A suture anchor for securing nearby tissue to bone, the suture anchor comprising:

an anchor body having an axis and a proximal end that is substantially transverse to the axis, wherein the anchor body further comprises a housing having a cavity at a proximal end thereof and an insert having a proximal end, the insert fitting substantially within the cavity of the housing, wherein the housing's cavity has a transverse cavity profile and wherein the insert has a transverse insert profile that is substantially the same as the transverse cavity profile, wherein the transverse cavity profile and the transverse insert profile are substantially square at proximal ends thereof, wherein at least one of the cavity and the insert has an axial profile that is substantially "U"-shaped;

a locking pin captured within the cavity to define a circuitous suture path running from a first side of the locking pin, around the locking pin, and to a second side of the locking pin;

an elongated suture puller slidably located within the circuitous suture path in the anchor body with first and second lengths extending from the anchor body, the second length including means for engaging suture;

means for anchoring the anchor body to the bone of the patient with the elongated suture puller extending from the anchor body;

suture connected to the second length of the elongated suture puller via the means for engaging, the suture being pulled into and through the circuitous suture path within the anchor body behind the elongated suture puller by the elongated suture puller being pulled outward therefrom via the first length;

a suture locking mechanism comprising a means for compressing suture within the circuitous path between the locking pin and the cavity that substantially prevents the suture from moving in at least a first direction after being pulled into and through the anchor body by the elongated suture puller;

a suture channel that extends through the insert from a first opening at the proximal end of the insert to a second opening at the same proximal end of the insert, wherein the suture channel is defined by a first suture channel that extends in the insert from a first side of the proximal end of the insert to a second side of the proximal end of the insert;

wherein the elongated suture puller is located in the suture channel until it is pulled therefrom; and wherein the elongated suture puller is an elongated, substantially flat band, and wherein the elongated suture puller's means for engaging suture is a notch that opens to a side thereof for pulling suture through the suture channel.

2. The suture anchor of claim 1 further comprising a suture puller channel for slidably receiving the elongated, substantially flat band.

3. The suture anchor of claim 2 wherein the suture puller channel is located in the insert, extends alone the suture channel from a first side of the proximal end of the insert to a second side of the proximal end of the insert, and opens into the suture channel.

4. The suture anchor of claim 3 wherein the suture channel is further defined by a second suture channel that opposes the first suture channel and that extends from a first side of the insert at the proximal end of the insert to a second side of the insert at the proximal end of the insert, the first and second suture channels accommodating the suture that is folded over on either side of the notch in the elongated suture puller.

5. A suture anchor for securing nearby tissue to bone, the suture anchor comprising:

an anchor body having an axis and a proximal end that is substantially transverse to the axis;

an elongated suture puller slidably located in the anchor body with first and second lengths extending from the anchor body, the second length including means for engaging suture;

means for anchoring the anchor body to the bone of the patient with the elongated suture puller extending from the anchor body;

suture connected to the second length of the elongated suture puller via the means for engaging, the suture being pulled into and through the anchor body behind the elongated suture puller by the elongated suture puller being pulled outward therefrom via the first length;

a suture locking mechanism that substantially prevents the suture from moving in at least a first direction after being pulled into and through the anchor body by the elongated suture puller;

wherein the anchor body comprises:
  a housing having a cavity at a proximal end thereof,
  an insert having a proximal end and a distal end, and first and second suture channels that extends through the insert, the insert fitting substantially within the cavity of the housing;
  a locking pin captured between the distal end of the insert and a bottom of the cavity to define a circuitous suture path running from the first suture channel, between a first side of the distal end of the insert and the locking pin, around the locking pin, between a second side of the distal end of the insert and the locking pin, to the second suture channel; and
  wherein the suture locking mechanism comprises means for compressing suture within the circuitous suture path between the distal end of the insert and the locking pin and between the locking pin and the cavity.

6. The suture anchor of claim 5 further comprises means for anchoring between the insert and the cavity.

7. A suture anchor for securing nearby tissue to bone, the suture anchor comprising:

an anchor body having an axis and a proximal end that is substantially transverse to the axis;

an elongated suture puller slidably located in the anchor body with first and second lengths extending from the anchor body, the second length including means for engaging suture;

means for anchoring the anchor body to the bone of the patient with the elongated suture puller extending from the anchor body;

suture connected to the second length of the elongated suture puller via the means for engaging, the suture being pulled into and through the anchor body behind the elongated suture puller by the elongated suture puller being pulled outward therefrom via the first length;

a suture locking mechanism that substantially prevents the suture from moving in at least a first direction after being pulled into and through the anchor body by the elongated suture puller;

a suture channel that extends through the anchor body from a first opening at the proximal end of the anchor body to a second opening at the same proximal end of the anchor body; and wherein the elongated suture puller is located in the suture channel until it is pulled therefrom;

wherein the anchor body comprises a housing having a cavity at a proximal end thereof and the anchor body further comprises an insert having a proximal end, the insert fitting substantially within the cavity of the housing;

wherein the housing's cavity has a transverse cavity profile and wherein the insert has a transverse insert profile that is substantially the same as the transverse cavity profile;

wherein the transverse cavity profile and the transverse insert profile are substantially square at proximal ends thereof;

wherein at least one of the cavity and the insert has an axial profile that is substantially "U"-shaped;

wherein the suture channel is defined by a first groove that extends around the insert from a first side of the proximal end of the insert to a second side of the proximal end of the insert;

wherein the elongated suture puller is an elongated, substantially flat band, and wherein the elongated suture puller's means for engaging suture is a notch that opens to a side thereof for pulling suture through the suture channel.

8. The suture anchor of claim 7 further comprising a suture puller channel for slidably receiving the elongated, substantially flat band.

9. The suture anchor of claim 8 wherein the suture puller channel is located between the insert and the housing, extends around the insert from a first side of the proximal end of the insert to a second side of the proximal end of the insert, opens into the suture channel, and extends laterally to either side of the suture channel.

10. The suture anchor of claim 9 wherein the suture channel is further defined by a second groove that opposes the first groove and that extends around the cavity from a first side of the cavity at the proximal end of the housing to a second side of the cavity at the proximal end of the housing, the first and second grooves accommodating the suture that is folded over on either side of the notch in the elongated suture puller.

* * * * *